US008608759B2

(12) United States Patent
Zaporojan et al.

(10) Patent No.: US 8,608,759 B2
(45) Date of Patent: Dec. 17, 2013

(54) MEDICAL DEVICES FOR SUTURING BIOLOGICAL TISSUE

(75) Inventors: Victor Zaporojan, Richardson, TX (US); Jian Q. Yao, Shanghai (CN); Rodney E. Bristol, Cedar Park, TX (US); Hui Liu, Austin, TX (US); Hali Wang, The Hills, TX (US); Hai-Qing Xian, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

(21) Appl. No.: 13/426,167

(22) Filed: Mar. 21, 2012

(65) Prior Publication Data

US 2012/0179173 A1 Jul. 12, 2012

Related U.S. Application Data

(62) Division of application No. 11/781,517, filed on Jul. 23, 2007, now Pat. No. 8,162,961.

(51) Int. Cl.
*A61B 17/04* (2006.01)

(52) U.S. Cl.
USPC .......................................... 606/148; 606/167

(58) Field of Classification Search
USPC ......... 606/139, 145–148, 198, 113, 150, 167, 606/170; 112/169
See application file for complete search history.

(56) References Cited

U.S. PATENT DOCUMENTS

| 3,835,859 | A | 9/1974 | Roberts et al. |
| 3,915,169 | A | 10/1975 | McGuire |
| 4,067,340 | A | 1/1978 | Le Noir |
| 4,344,193 | A | 8/1982 | Kenny |
| 4,493,323 | A | 1/1985 | Albright et al. |
| 5,320,633 | A | 6/1994 | Allen et al. |
| 5,334,214 | A | 8/1994 | Putnam |

(Continued)

FOREIGN PATENT DOCUMENTS

| DE | 4403602 A1 | 8/1995 |
| WO | WO-03/077771 A1 | 9/2003 |

(Continued)

OTHER PUBLICATIONS

"U.S. Appl. No. 11/781,517, Examiners Interview Summary mailed Nov. 2, 2011", 3 pgs.

(Continued)

*Primary Examiner* — Thomas McEvoy
(74) *Attorney, Agent, or Firm* — Schwegman, Lundberg & Woessner P.A.

(57) ABSTRACT

Medical devices for cutting and suturing biological tissue generally include a shaft and first and second guide members each including a first portion coupled to the shaft at a first location and a second portion coupled to the shaft at a second location. The first portions are movable along the shaft relative to the second portions, and the first and second guide members define an arcuate profile and are configured to flex in response to such movement. When used to cut tissue, the medical device may further include a blade positioned between the first and second guide members. When used to suture tissue, one or more suture guides may be provided on the first guide member for directing a suture needle through tissue proximate the first guide member. Methods of repairing and replacing a meniscus using the medical devices are also provided.

16 Claims, 16 Drawing Sheets

(56) References Cited

U.S. PATENT DOCUMENTS

| | | | |
|---|---|---|---|
| 5,372,146 A | 12/1994 | Branch | |
| 5,443,474 A | 8/1995 | Sfakianos et al. | |
| 5,520,691 A | 5/1996 | Branch | |
| 5,562,683 A | 10/1996 | Chan | |
| 5,562,687 A | 10/1996 | Chan | |
| 5,649,947 A | 7/1997 | Auerbach et al. | |
| 5,713,863 A * | 2/1998 | Vigil et al. | 604/104 |
| 5,735,903 A | 4/1998 | Li et al. | |
| 5,772,676 A | 6/1998 | Cuschieri et al. | |
| 5,823,994 A | 10/1998 | Sharkey et al. | |
| 5,865,849 A | 2/1999 | Stone | |
| 5,913,900 A | 6/1999 | Stone | |
| 5,928,252 A | 7/1999 | Steadman et al. | |
| 5,954,747 A | 9/1999 | Clark | |
| 5,984,858 A | 11/1999 | Stone | |
| 6,046,379 A | 4/2000 | Stone et al. | |
| 6,093,204 A | 7/2000 | Stone | |
| 6,231,608 B1 | 5/2001 | Stone | |
| 6,306,156 B1 | 10/2001 | Clark | |
| 6,368,335 B1 | 4/2002 | Chan | |
| 6,443,963 B1 | 9/2002 | Baldwin et al. | |
| 6,455,309 B2 | 9/2002 | Stone | |
| 6,629,984 B1 | 10/2003 | Chan | |
| 6,758,865 B1 | 7/2004 | Stone et al. | |
| 6,793,676 B2 | 9/2004 | Plouhar et al. | |
| 6,884,249 B2 | 4/2005 | May et al. | |
| 6,972,027 B2 | 12/2005 | Fallin et al. | |
| 6,994,730 B2 | 2/2006 | Posner | |
| 7,108,700 B2 | 9/2006 | Chan | |
| 7,153,312 B1 | 12/2006 | Torrie et al. | |
| 2001/0002446 A1 | 5/2001 | Plouhar et al. | |
| 2002/0019640 A1 | 2/2002 | McGuckin, Jr. | |
| 2002/0111647 A1* | 8/2002 | Khairkhahan et al. | 606/200 |
| 2002/0138097 A1* | 9/2002 | Ostrovsky et al. | 606/200 |
| 2004/0087942 A1 | 5/2004 | McGuckin, Jr. et al. | |
| 2004/0116843 A1 | 6/2004 | Chan | |
| 2004/0243250 A1 | 12/2004 | Stone et al. | |
| 2004/0267270 A1 | 12/2004 | Jacobs et al. | |
| 2005/0033325 A1 | 2/2005 | May et al. | |
| 2005/0070890 A1 | 3/2005 | Nobis et al. | |
| 2005/0090840 A1 | 4/2005 | Gerbino et al. | |
| 2005/0234549 A1 | 10/2005 | Kladakis et al. | |
| 2005/0283170 A1 | 12/2005 | Battles et al. | |
| 2005/0283192 A1 | 12/2005 | Torrie et al. | |
| 2006/0064126 A1 | 3/2006 | Fallin et al. | |
| 2006/0178680 A1 | 8/2006 | Nelson et al. | |
| 2007/0027476 A1 | 2/2007 | Harris et al. | |
| 2007/0038230 A1 | 2/2007 | Stone et al. | |
| 2009/0030431 A1 | 1/2009 | Zaporojan et al. | |

FOREIGN PATENT DOCUMENTS

| | | |
|---|---|---|
| WO | WO-2005016175 A2 | 2/2005 |
| WO | WO-2006/064025 A2 | 6/2006 |
| WO | WO-2007020449 A2 | 2/2007 |

OTHER PUBLICATIONS

"U.S. Appl. No. 11/781,517, Final Office Action mailed Jun. 10, 2011", 11 pgs.

"U.S. Appl. No. 11/781,517, Non Final Office Action mailed Jan. 20, 2011", 9 pgs.

"U.S. Appl. No. 11/781,517, Notice of Allowance mailed Dec. 27, 2011", 7 pgs.

"U.S. Appl. No. 11/781,517, Response filed Jan. 5, 2011 to Restriction Requirement mailed Dec. 7, 2010", 8 pgs.

"U.S. Appl. No. 11/781,517, Response filed Mar. 31, 2011 to Non-Final Office Action mailed Jan. 20, 2011", 12 pgs.

"U.S. Appl. No. 11/781,517, Response filed Nov. 10, 2011 to Final Office Action mailed Jun. 10, 2011", 12 pgs.

"U.S. Appl. No. 11/781,517, Restriction Requirement mailed Dec. 7, 2010", 8 pgs.

"International Application Serial No. PCT/US2008/070406, International Search Report and Written Opinion mailed Jun. 5, 2009", 17 pgs.

* cited by examiner

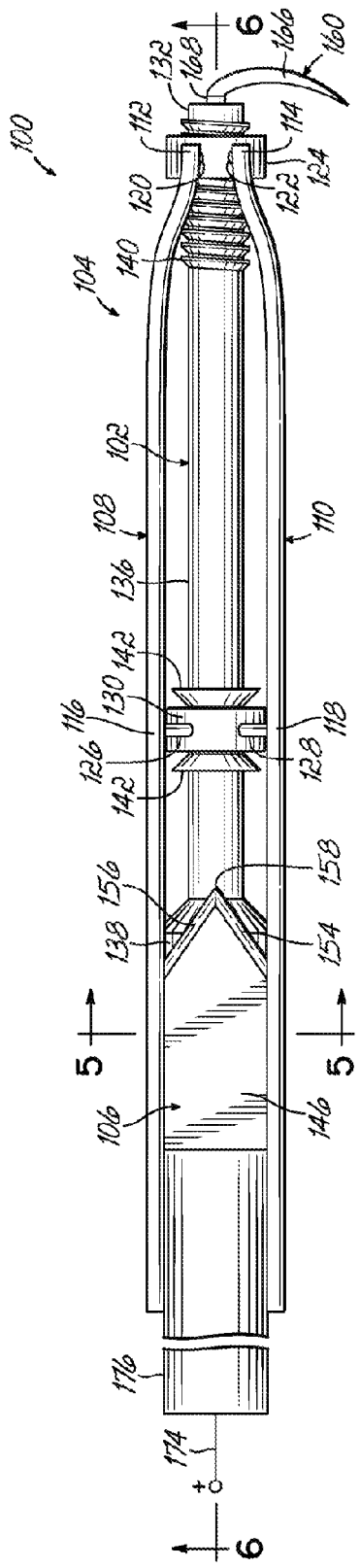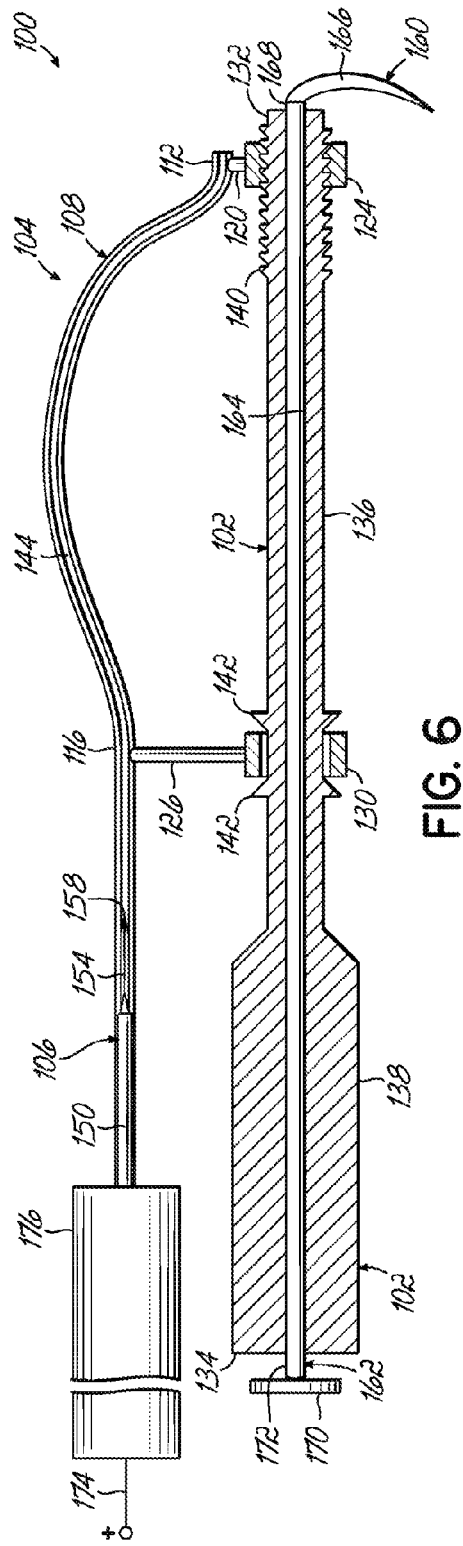

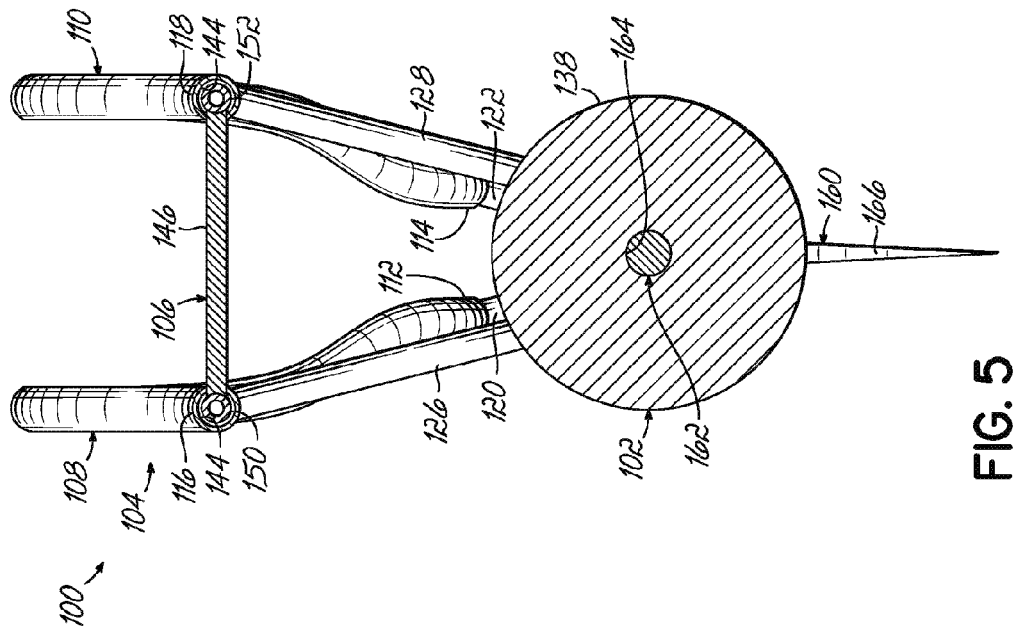
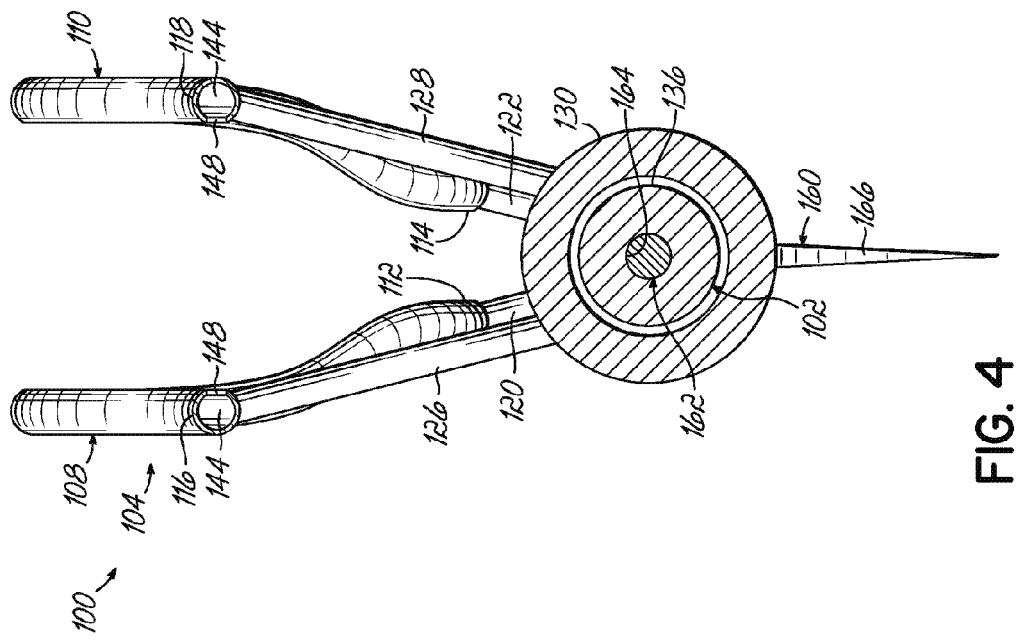
FIG. 5
FIG. 4

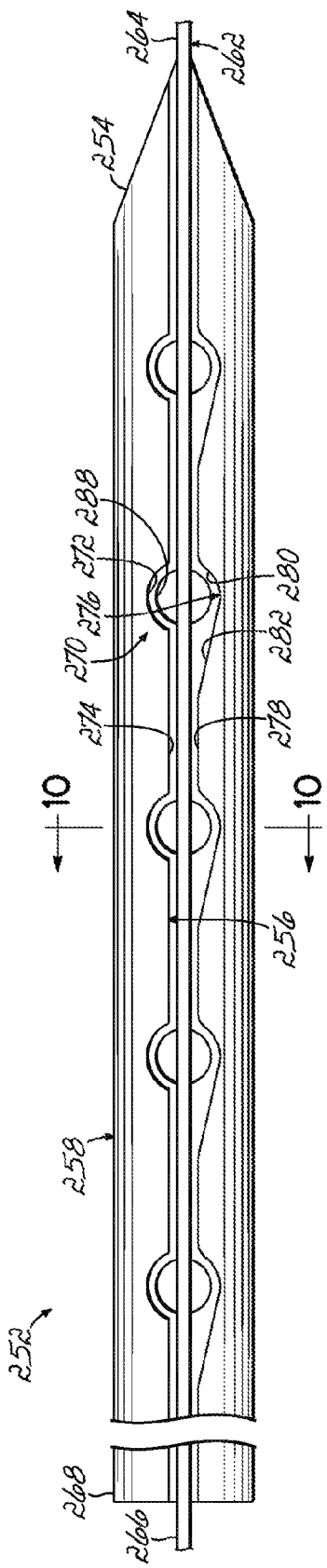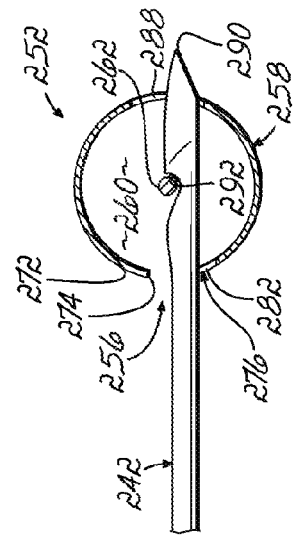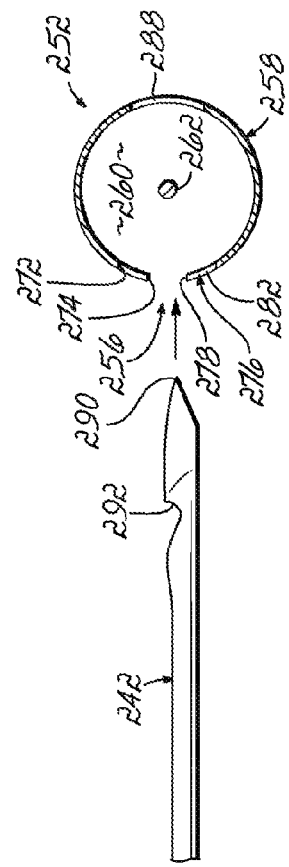

MEDICAL DEVICES FOR SUTURING BIOLOGICAL TISSUE

CROSS-REFERENCE TO RELATED APPLICATION AND CLAIM OF PRIORITY

This patent matter is a divisional of and claims priority to U.S. patent application Ser. No. 11/781,517, now issued as U.S. Pat. No. 8,162,961, entitled "MEDICAL DEVICES AND METHODS FOR CUTTING AND SUTURING BIOLOGICAL TISSUE," filed on Jul. 23, 2007, the specification of which is incorporated herein in its entirety by reference.

TECHNICAL FIELD

Medical devices and methods, more particularly, medical devices and methods for cutting and suturing biological tissue.

BACKGROUND

A human knee includes a lateral meniscus and a medial meniscus positioned between the joint surfaces of the femur and tibia. Each meniscus is a crescent or C-shaped piece of cartilage having a generally wedge-like or triangular cross-section that tapers inwards. In other words, the outer peripheral portion of each meniscus is relatively thick while the inner peripheral portion is relatively thin. Such an arrangement provides a "cup" for the curved bottom surface of the femur, which would otherwise move on the flat upper surface of the tibia with little joint stability. The menisci also play an important role in shock absorption and lubrication.

The outer peripheral portion of each meniscus is attached to the tibia by short coronary ligaments while the inner peripheral portion is not. Blood flows only to the outer peripheral portion from small arteries around the knee joint. As a result, the outer peripheral portion is sometimes referred to as a "red zone" and the remainder of the meniscus is referred to as a "white zone." Because a meniscus is largely avascular (i.e., has a large white zone), it can be difficult for the body to heal tears not confined to the outer one-third of the meniscus.

The menisci may be torn when the knee experiences sudden and severe loads or as a result of degeneration. When a tear is located in the red zone, a surgeon may be able to repair it by suturing the tissue that forms the meniscus. More often, however, the torn portion requires removal because the tear is not limited to such an area. Repairing a small tear in the white zone of the meniscus is generally not effective because of the tissue's inability to heal even if sewn together. Typically, the portion of the meniscus with the tear is cut using small instruments and removed from the knee. The remainder of the meniscus is then balanced and contoured to provide a gradually tapered transition into the area of the resection.

Although some attempts have been made to replace the removed portion of a meniscus with an implant, there remains significant room for improvement. Many of the implants themselves have limited effectiveness, and the surgical procedures associated with them are often time-consuming, challenging, and not particularly suited for arthroscopic techniques.

SUMMARY

Medical devices and methods for cutting and suturing biological tissue are described below. The devices and methods are particularly suited for cutting and suturing the cartilage tissue forming the meniscus of a knee joint, although the devices and methods may be used in connection with other tissue in a patient's body.

In one embodiment, a medical device for cutting biological tissue generally comprises a shaft having a distal end, first and second guide members each including a first portion coupled to the shaft at a first location and a second portion coupled to the shaft at a second location spaced from the first location, and a blade positioned between the first and second guide members. The first and second guide members define a cutting path and are configured to direct the blade along at least a portion of the cutting path to cut the biological tissue. Because the first portion of the first guide member and the first portion of the second guide member are movable along the shaft relative to the second location, the first and second guide members are configured to flex upon such movement to change a profile of the cutting path. The cutting path may be defined by a linear section, an arcuate section, or combinations thereof.

In another embodiment, a medical device for cutting biological tissue generally comprises a shaft, a cutting guide, and a blade. The cutting guide includes a first collar received on the shaft at a first location, a second collar retained on the shaft at a second location spaced from the first location, and first and second guide members each coupled to the first collar and the second collar. The blade is positioned between the first and second guide members, which are configured to direct the blade along at least a portion of an arcuate cutting path to cut the biological tissue. In a further embodiment, the shaft includes a threaded portion and the first collar member is threadably received on the threaded portion. Rotating the shaft relative to the cutting guide causes the first collar to move along the shaft relative to the second collar, with the first and second guide members flexing in response to such movement to change a profile of the arcuate cutting path.

One embodiment of a medical device for suturing biological tissue generally comprises a shaft and a first guide member, with the first guide member including a first portion coupled to the shaft at a first location and a second portion coupled to the shaft at a second location spaced from the first location. The first guide member is configured to be positioned proximate the biological tissue and further includes at least one suture guide configured to direct a suture needle along a path extending through the tissue. The first guide member also has an arcuate profile. Because the first portion of the first guide member is movable along the shaft relative to the second location, the first guide member is configured to flex upon such movement to change an arcuate profile thereof.

Another embodiment of a medical device for suturing biological tissue generally comprises a shaft having a threaded portion, a first collar threadably received on the threaded portion of the shaft, and a second collar retained on the shaft at a location spaced from the threaded portion. A first guide member having an arcuate profile includes a first portion coupled to the first collar, a second portion coupled to the second collar, and at least one suture guide configured to direct the suture needle along a path extending through tissue proximate the first guide member. The shaft is rotatable relative to the first guide member to move the first collar along the shaft relative to the second collar, and the first guide member is configured to flex upon such movement to change an arcuate profile thereof.

The medical devices for suturing biological tissue may further include an external needle guide having first and second portions positioned proximate the respective first and second locations on the shaft. The external needle guide may be arranged so that the biological tissue is located between the external needle guide and the first guide member, and may be configured to receive the suture needle after the suture needle passes through the tissue.

In still another embodiment, a medical device for repairing or replacing biological tissue is provided. This medical device generally includes a shaft, first and second guide members each having a first portion coupled to the shaft at a first location and a second portion coupled to the shaft at a second location spaced from the first location, and a blade positioned between the first and second guide members. The first guide member is configured to be positioned proximate the biological tissue and further includes at least one suture guide configured to direct the suture needle along a path extending through the tissue. Additionally, the first and second guide members are configured to direct the blade along at least a portion of an arcuate cutting path.

A method of replacing part of a damaged meniscus is also provided in which an implant from the meniscus of a donor is used. The method generally comprises cutting off a portion of the damaged meniscus to expose the vascular structure of the remainder of the meniscus along a cutting plane. An image of the vascular structure along the cutting plane is then taken and compared to the vascular structure of at least one implant. For example, several implants may be available and the image of the damaged meniscus along the cutting plane may be compared to each. The implant with the closest vascular structure to that of the remainder of the damaged meniscus is then selected and eventually secured to the remainder of the damaged meniscus.

BRIEF DESCRIPTION OF THE DRAWINGS

The accompanying drawings, which are incorporated in and constitute a part of this specification, illustrate exemplary embodiments of the invention and, together with the summary given above, and the detailed description given below, serve to explain the invention.

FIG. 3 is a top elevational view of the cutting device shown in FIG. 2.

FIG. 4 is a cross-sectional view taken along line 4-4 in FIG. 2.

FIG. 5 is a cross-sectional view taken along line 5-5 in FIG. 3.

FIG. 6 is a cross-sectional view taken along line 6-6 in FIG. 3.

FIG. 9 is a side elevational view of a portion of an external needle guide for the suturing device shown in FIG. 7.

FIGS. 10-12 are cross-sectionals view taken along line 10-10 in FIG. 9 sequentially illustrating a suture needle pulling suture thread from the external needle guide.

DETAILED DESCRIPTION

Figure 1:
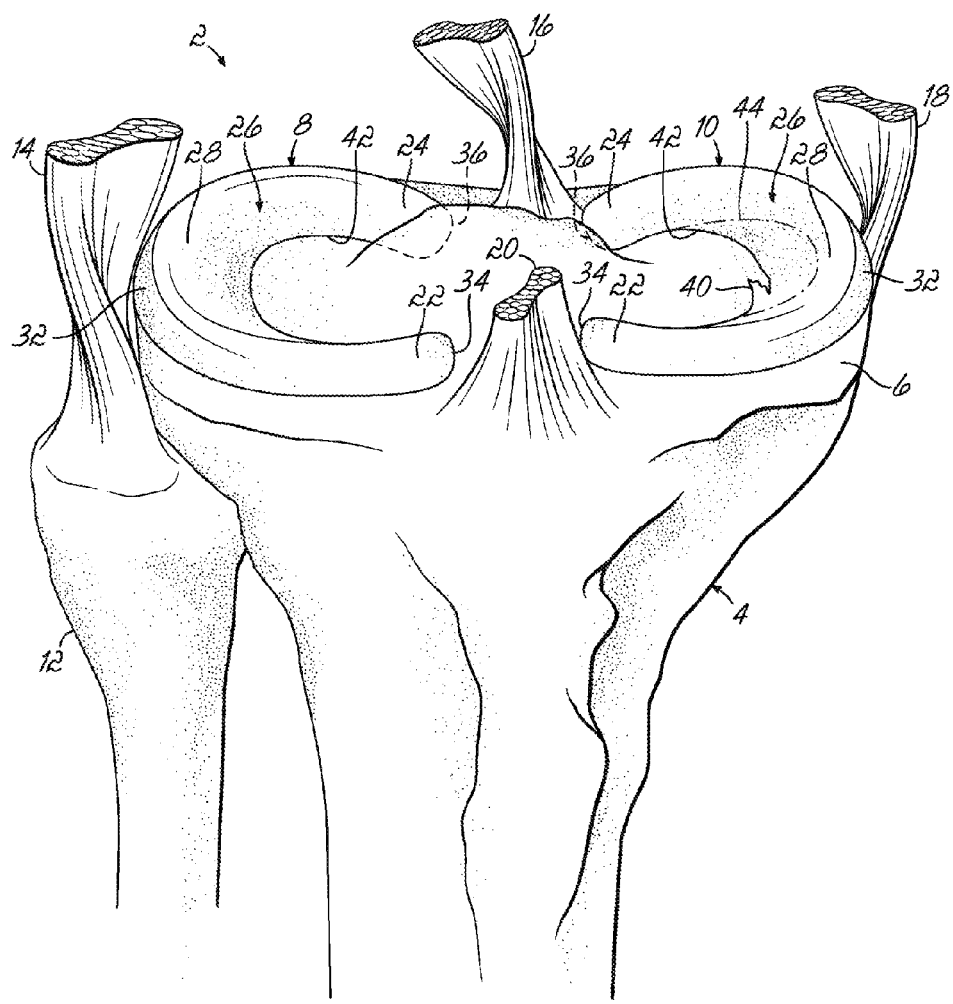
FIG. 1 is a perspective view showing a portion of the anatomy of a knee joint.

With reference to FIG. 1, the anatomy of a portion of a knee joint 2 is generally shown. The knee joint 2 includes a tibia 4 having a joint surface 6 supporting a lateral meniscus 8 and a medial meniscus 10. The lateral meniscus 8 and medial meniscus 10 are each a substantially crescent or C-shaped piece of cartilage that helps support and stabilize a femur (not shown) on the joint surface 6. A fibula 12 is also shown in FIG. 1, along with a lateral collateral ligament 14, a posterior cruciate ligament 16, a medial collateral ligament 18, and an anterior cruciate ligament 20.

Various devices and methods for cutting and/or suturing the lateral meniscus 8 or medial meniscus 10 are described in further detail below. It will be appreciated, however, that the devices and methods may equally apply to other areas of a patient's body. Thus, although further reference will be made to the anatomy of the knee joint 2, those skilled in the art will appreciate that the cartilage forming the lateral meniscus 8 or medial meniscus 10 is merely one example of biological tissue that may be cut and/or sutured using the devices and methods described below.

Figure 22:
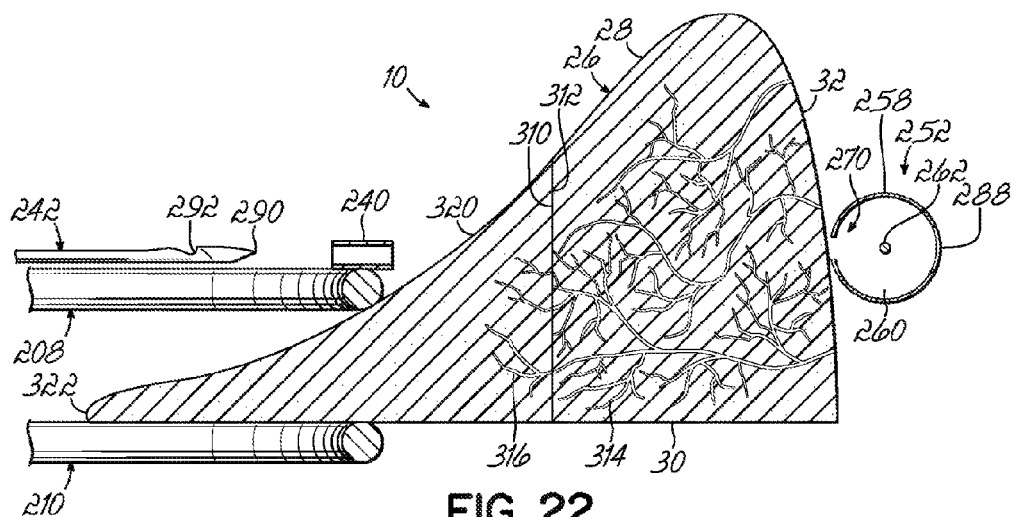
FIGS. 22-24 are cross-sectional side views showing a suture needle pulling suture thread through the lateral meniscus.
Figure 23:
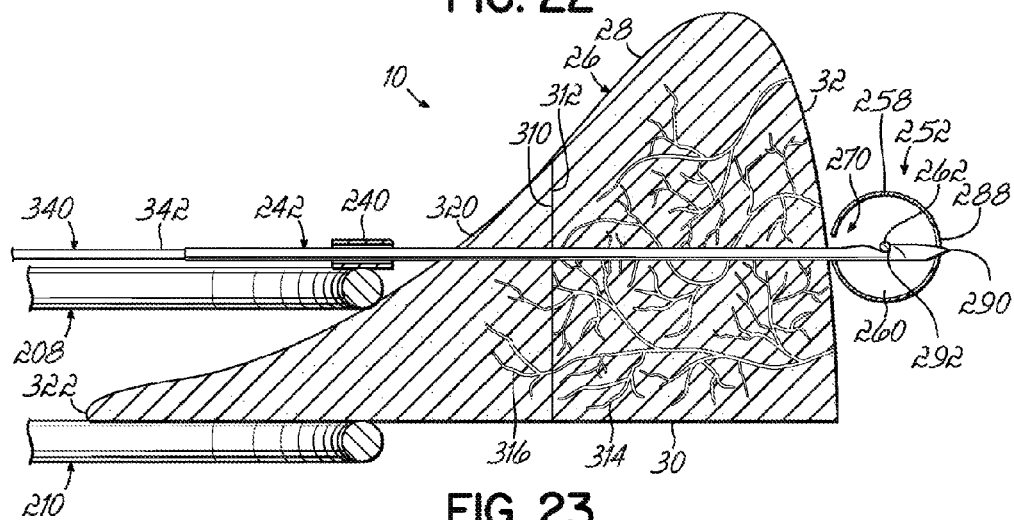
Figure 24:
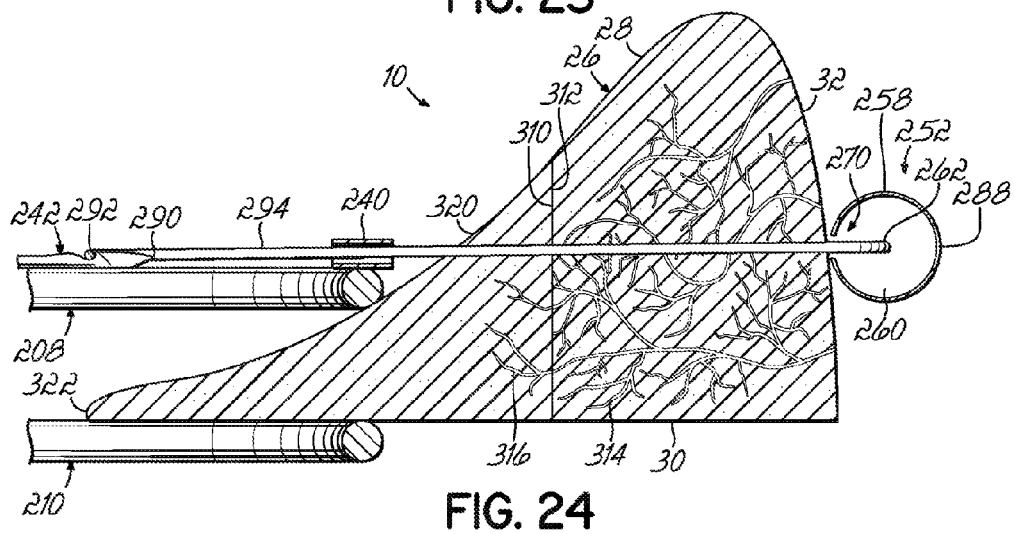

Still referring to FIG. 1, the lateral meniscus 8 and medial meniscus 10 each include an anterior horn (front portion) 22, a posterior horn (rear portion) 24, and a body 26 positioned between the anterior horn 22 and posterior horn 24. The body 26 has a wedge-shaped cross-section with a superior surface 28 facing the femur, an inferior surface 30 (FIGS. 22-24) facing the tibia 4, and a lateral surface 32 extending between the superior surface 28 and inferior surface 30. Short coronary ligaments (not shown) attach the lateral surface 32 to the tibia 4 and femur. Although an end 34 of the anterior horn 22 and an end 36 of the posterior horn 24 are normally attached to the joint surface 6, most of the inferior surface 30 is not attached to the tibia 4.

Figure 1A:
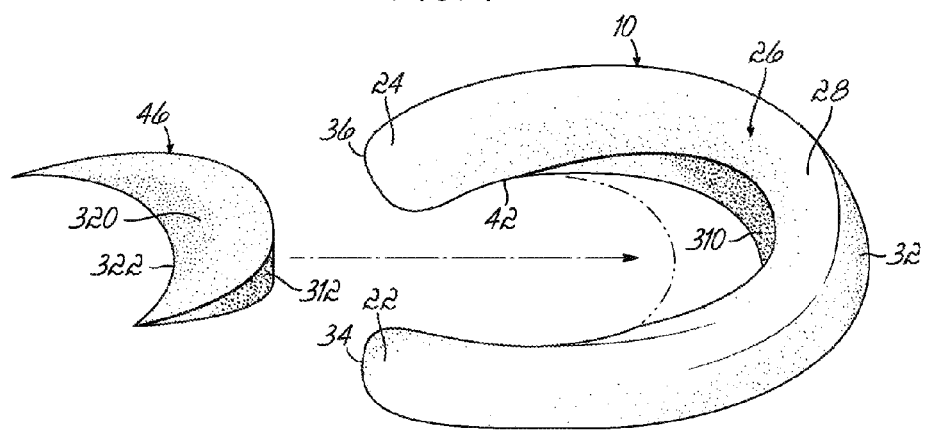
FIG. 1A is a perspective view showing a medial meniscus of the knee joint in FIG. 1 and an implant for replacing part of the medial meniscus.

When a tear 40 or other defect is located at or near an inner edge 42 of the lateral meniscus 8 or medial meniscus 10, it may be desirable or necessary to remove a damaged portion 44 of the meniscus surrounding the tear 40. This typically requires cutting the cartilage (i.e., fibrous connective tissue) forming the associated meniscus. Once removed, the damaged portion 44 may be replaced by an implant 46, as shown in FIG. 1A. The implant 46 may be any suitable structure (i.e., whether synthetic and/or natural material) configured to cooperate with the remainder of the lateral meniscus 8 or medial meniscus 10. However, the discussion below will focus on the implant 46 being an allograft or xenograft harvested or cut from a donor meniscus.

Referring now to FIGS. 2-6, one embodiment of a cutting device 100 for cutting the lateral meniscus 8, medial meniscus 10, or other biological tissue in a patient's body is shown. The cutting device 100 generally comprises a shaft 102, a cutting guide 104 coupled to the shaft 102, and a blade 106 associated with the cutting guide 104. The cutting guide 104 is defined by a first guide member 108 and a second guide member 110. A first portion 112 of the first guide member 108 and a first portion 114 of the second guide member 110 are coupled to the shaft 102 at a first location. Similarly, a second portion 116 of the first guide member 108 and a second portion 118 of the second guide member 110 are coupled to the shaft 102 at a second location spaced from the first location. Any suitable coupling arrangement or technique may be used. In the exemplary embodiment shown in FIGS. 2-6, an arm 120 couples the first portion 112 to a first collar 124 received on the shaft 102 at the first location. An arm 122 likewise couples the first portion 114 to the first collar 124. Similarly, an arm 126 and an arm 128 may couple the second portion 116 and second portion 118, respectively, to a second collar 130 retained on the shaft 102 at the second location.

The first guide member 108 and second guide member 110 are each constructed from a flexible material. As shown in FIG. 2A, the first guide member 108 and second guide member 110 are generally straight (i.e., linear) when the cutting guide 104 is not coupled to the shaft 102. Because the lengths of arm 120 and arm 122 are shorter than the lengths of arm 126 and arm 128, the first collar 124 is normally aligned along a first axis 125 and the second collar 130 is normally aligned along a second axis 127. The first axis 125 is spaced from the second axis 127 by an offset distance "D1" measured along the first axis 125 and, when in this initial configuration, the first collar 124 is spaced from the second collar 130 by an axial distance "D2" measured along the second axis 127.

After loading the second collar 130 onto the shaft 102, the first collar 124 is brought into alignment with the second axis 127 and loaded onto the shaft 102 as well. The first guide member 108 and second guide member 110 allow the first collar 124 to be moved in such a manner due to their flexible nature. In particular, as the first collar 124 is brought into alignment with the second axis 127 and moved slightly toward the second collar 130, the first guide member 108 bows (i.e., curves) outwardly between arm 120 and arm 126, and the second guide member 110 bows outwardly between arm 122 and arm 128. The first collar 124 is spaced from the second collar 130 by an axial distance "D3" when received on the shaft 102, with D3 being less than D2.

In an alternative embodiment, the lengths of arm 126 and arm 128 may be approximately equal to the lengths of arm 120 and arm 122 such that the first collar 124 and second collar 130 are normally aligned along the first axis 125. Such an arrangement may facilitate inserting the cutting guide 104 into the patient's body, especially if the lengths of arms 120, 122, 126, and 128 are relative short. Indeed, if desired, the first collar 124 and second collar 130 may each be directly coupled to the first guide member 108 and second guide member 110 such that the arms 120, 122, 126, and 128 are not required. In either of these alternative configurations, the need to bring the first collar 124 into alignment with the second collar 130 is eliminated, which may also facilitate the assembly of the cutting device 100. Additionally, the first collar 124 and second collar 130 may remain spaced apart from each other by the axial distance D2 when received on the shaft 102 so that the first guide member 108 and second guide member 110 remain generally straight (i.e., linear). The cutting device 100 could then be used in a manner similar to that described below to cut tissue along a generally straight or linear cutting path.

Still referring to FIGS. 2-6, the shaft 102 includes a distal end 132 and a proximal end 134, and may be defined by a first section 136 having a first diameter and a second section 138 having an enlarged, second diameter. A threaded portion 140 is provided on the first section 136 proximate the distal end 132 so that the first collar 124 is threadably received on the shaft 102. The second collar 130, on the other hand, is slidably received on the first section 136. Because the second collar 130 is retained on the shaft 102 at a location spaced from the threaded portion 140, rotating the shaft 102 relative to the cutting guide 104 moves the first collar 124 along the shaft 102 (i.e., in an axial direction) relative to the second collar 130. For example, in one embodiment, the second collar 130 is retained by horns 142 provided on the shaft 102 on opposite sides of the second collar 130. The horns 142 may be formed integrally with the shaft 102 or may be separate components mounted on the shaft 102. If integrally formed, a gap (not shown) may be provided in the second collar 130 so that the second collar 130 may be snap-fit onto the shaft 102 between the horns 142. If mounted on the shaft 102 on opposite sides of the second collar 130, the horns 142 prevent the second collar 130 from moving axially along the shaft 102. The position of the horns 142 may be set relative to the distal end 132 of the shaft 102 so that the first guide member 108 and second guide member 110 have a desired profile when the first collar 124 is first received on the threaded portion 140 proximate the distal end 132.

The blade 106 is positioned between the first guide member 108 and second guide member 110, which define an arcuate cutting path. The first guide member 108 and second guide member 110 are configured flex upon movement of the first collar 124 relative to the second collar 130. The first guide member 108 and the second guide member 110 are also configured to direct the blade 106 along at least a portion of the arcuate cutting path. For example, as shown in FIGS. 3-5, the first guide member 108 and second guide member 110 may each include a substantially C-shaped cross section defining an internal channel 144. A body 146 of the blade 106 extends through gaps 148 in the first guide member 108 and second guide member 110 so that a first rail 150 and a second rail 152 provided on opposite sides of the body 146 are each received in the corresponding internal channel 144. Such a configuration allows the blade 106 to be securely positioned and advanced along the arcuate path defined by the first guide member 108 and second guide member 110.

However, it will be appreciated that a wide variety of other configurations are possible to achieve this same effect. For example, the first guide member 108 and second guide member 110 need not have a substantially C-shaped cross-section and instead may further include one or more attachments (not shown) each having a cup-shaped or otherwise concave surface for supporting the first rail 150 or second rail 152. A plurality of such attachments may be provided on both the first guide member 108 and the second guide member 110 to direct the blade 106 along the arcuate cutting path. Alternatively, the first guide member 108 and second guide member 110 may each include a single, elongate attachment (not shown) aligned along a length thereof. In another embodiment, the blade 106 may be coupled to one or more full or partial collars (not shown) slidably received on the first guide member 108 and second guide member 110. In still another embodiment, the blade 106 may be coupled to one or more rollers (not shown). The rollers may direct the blade along respective tracks defined by the first guide member 108 and second guide member 110.

Regardless of the manner in which the first guide member 108 and second guide member 110 are configured to support and direct the blade 106, tissue positioned in the arcuate cutting path is cut by the blade 106 as the blade 106 is advanced along the arcuate cutting path. A first sharp edge 154 and a second sharp edge 156 of the blade 106 converge toward a point or tip 158 to facilitate this cutting operation. Those skilled in the art will appreciate that alternative configurations of the blade 106 are possible as well, including, for example, configurations in which the blade 106 has only a single sharp edge (not shown).

FIGS. 4 and 5 illustrate arm 126 and arm 128 being angled relative to each other. In other words, arm 126 and arm 128 each extend away from the second collar 130 in different directions so that an angle is defined between arm 126 and arm 128. For example, arm 126 may extend away from the second collar 130 at an angle of approximately 45° relative to arm 128. Arm 120 and arm 122 may be angled relative to each other in a similar manner. Those skilled in the art will appreciate that the angle between arm 120 and arm 122 and the angle between arm 126 and arm 128 may be selected to provide the desired spacing between and orientation of the first guide member 108 and second guide member 110. Additionally, those skilled in the art will further appreciate that other configurations are possible to couple the cutting guide 104 to the shaft 102 while positioning the first guide member 108 and second guide member 110 a desired distance relative to each other. For example, in an alternative embodiment, arm 126 and arm 128 may be coupled to a common stem portion (not shown) extending from the second collar 130 so as to define a substantially Y-shaped support for the first guide member 108 and second guide member 110.

Figure 2:
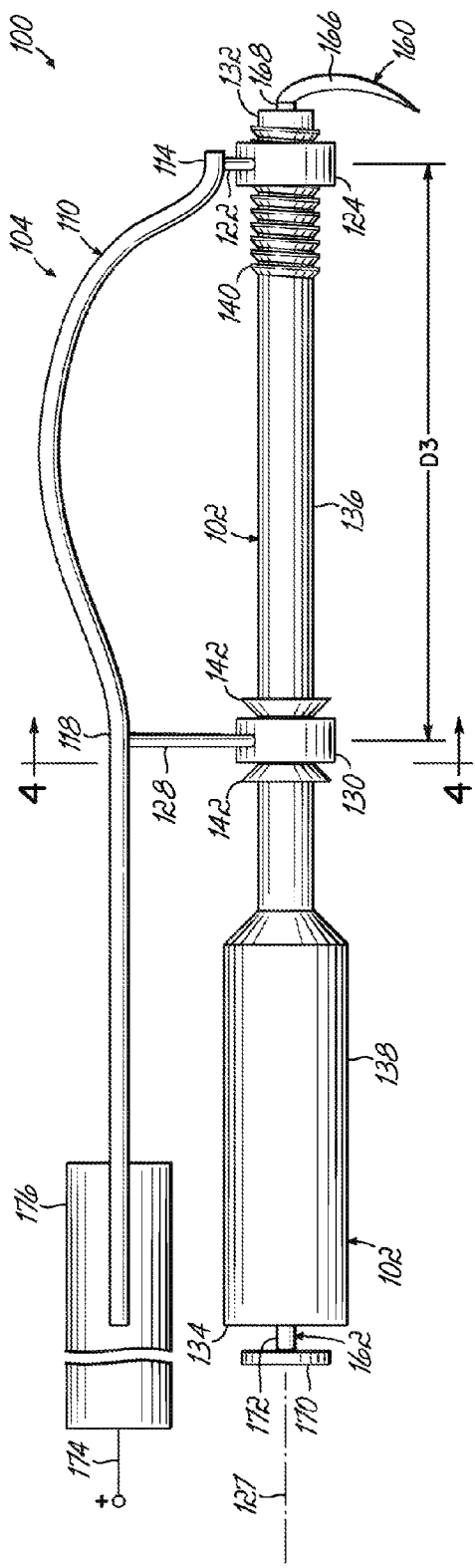
FIG. 2 is a side elevational view of a cutting device according to one embodiment for cutting biological tissue.
Figure 2A:
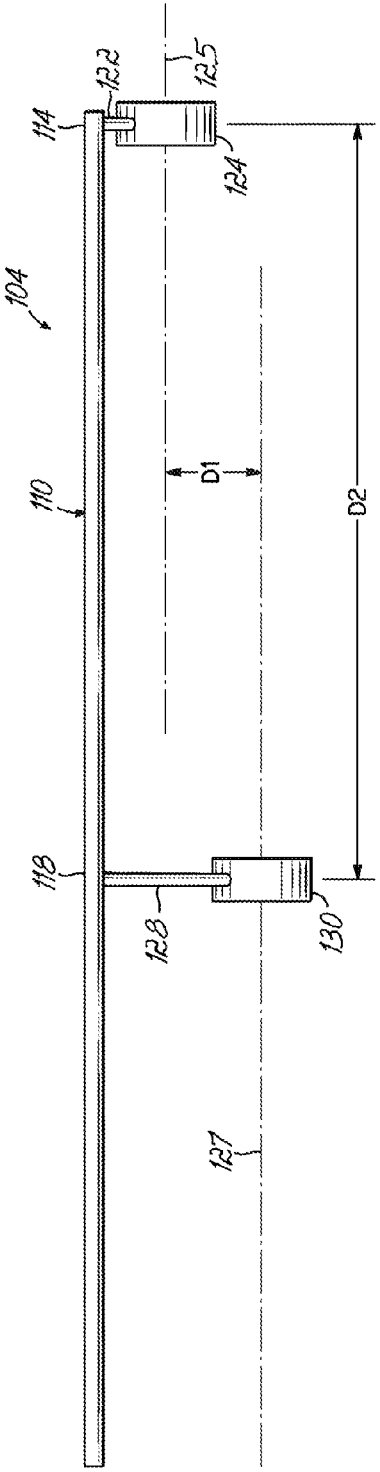
FIG. 2A is a side elevational view of a cutting guide of the cutting device shown in FIG. 2.

As best shown in FIGS. 2, 3, and 6, the cutting device 100 may further include an attachment member 160 to secure the cutting device 100 relative to the tissue to be cut. In one embodiment, the attachment member 160 includes a rod 162 extending through a bore 164 provided in the shaft 102 and a hook 166 coupled to a distal end 168 of the rod 162. The hook 166 extends at an angle from the rod 162 and is configured to "dig in" or catch onto tissue or other structure. To prevent the shaft 102 from sliding off the attachment member 160, a handle 170 having a larger diameter than the bore 164 is coupled to a proximal end 172 of the rod 162. The handle 170 may be screwed, mounted, or otherwise attached to the proximal end 172 after the rod 162 is loaded through the bore 164 from the distal end 132 of the shaft 102.

Thus, once secured with tissue positioned between the first guide member 108 and second guide member 110, the shaft 102 may be rotated relative to the cutting guide 104 to move the first collar 124 relative to the second collar 130. The second section 138 of the shaft 102 serves as a handle to facilitate this rotation. Additionally, the first guide member 108 and second guide member 110 are configured to flex in response to the relative movement between the first collar 124 and the second collar 130 to adjust the profile of the arcuate cutting path. Once the desired profile is attained, the blade 106 is advanced along the first guide member 108 and second guide member 110 to cut the tissue along the arcuate cutting path. A wire 174 surrounded by protective insulation 176 may be coupled to the blade 106 to heat the blade 106 and thereby facilitate this cutting operation. This electrocautery technique and other known electrosurgical techniques may be readily incorporated into the cutting device 100.

As can be appreciated, the relative movement between the first collar 124 and second collar 130 may be accomplished using a number of other alternative arrangements not shown in FIGS. 2-6. For example, although FIGS. 2-6 illustrate the threaded portion 140 being proximate the distal end 132 of the shaft 102, the threaded portion 140 may alternatively be provided proximate the second section 138 or elsewhere on the shaft 102. In such an embodiment, the second collar 130 may be threadably received on the threaded portion 140 and the first collar 124 may be retained on the shaft 102 at the distal end 132 by structure similar to the horns 142. Rotating the shaft 102 relative to the cutting guide 104 would move the second collar 130 along the shaft 102 in an axial direction toward or away from the first collar 124. The first guide member 108 and second guide member 110 would then flex in response to this movement in the same manner as described above.

Figure 7:
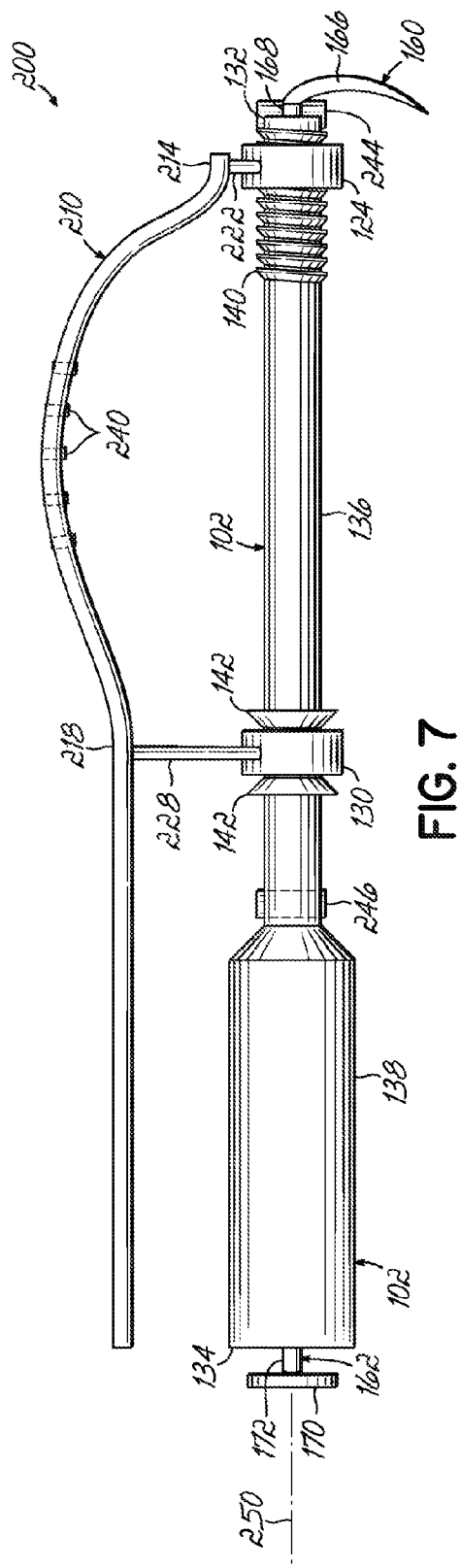
FIG. 7 is a side elevational view of a suturing device according to one embodiment for suturing biological tissue.
Figure 8:
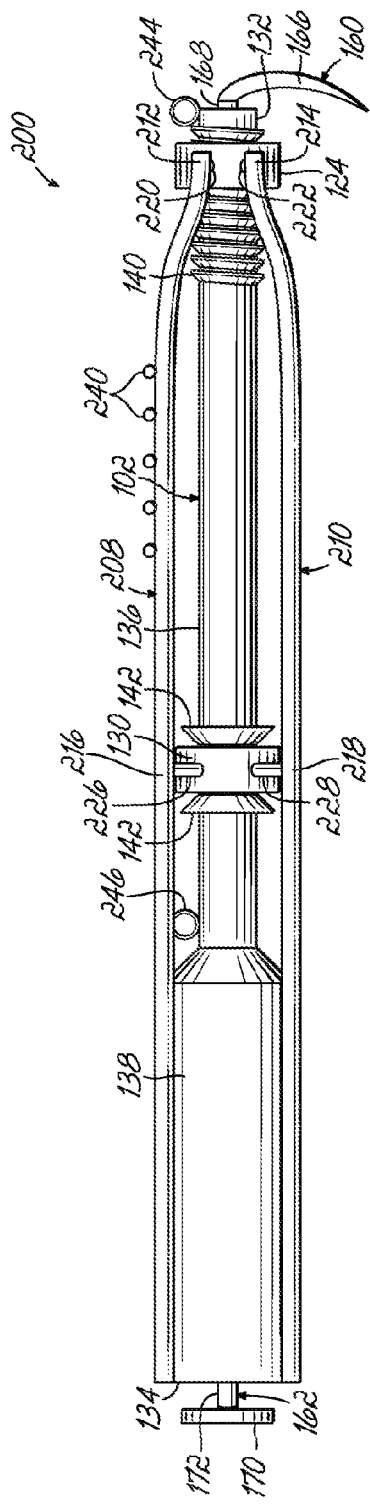
FIG. 8 is a top elevational view of the suturing device shown in FIG. 7.

With reference to FIGS. 7 and 8, one embodiment of a suturing device 200 for suturing tissue is shown. The suturing device 200 has a similar structure as the cutting device 100. Accordingly, like reference numbers are used in FIGS. 7 and 8 to refer to like structure from the cutting device 100 shown in FIGS. 2-6.

To this end, the suturing device 200 includes the shaft 102, the first collar 124, and second collar 130. A first guide member 208 and a second guide member 210 are each coupled to the first collar 124 and the second collar 130 in the same manner as the first guide member 108 and second guide member 110, respectively (FIGS. 2-6). In other words, a first portion 212 of the first guide member 208 and a first portion 214 of the second guide member 210 are respectively coupled to the first collar 124 by an arm 220 and an arm 222. Similarly, a second portion 216 of the first guide member 208 and a second portion 218 of the second guide member 210 are respectively coupled to the second collar 130 by an arm 226 and an arm 228. The lengths of arm 220 and arm 222 may be substantially the same or different than the lengths of arm 226 and 226 depending on whether generally straight or arcuate profiles of the first guide member 208 and second guide member 210 are desired (see discussion above with respect to FIG. 2A). Alternatively, the first guide member 208 and second guide member 210 may each be directly coupled to the first collar 124 and second collar 130. The first guide member 208 and second guide member 210 differ from the first guide member 108 and second guide member 110 in that the latter need not be configured to position and direct the blade 106 (FIGS. 3-6). As discussed below, however, a single device for both cutting and suturing tissue—and thus combining aspects of both the cutting device 100 and suturing device 200—is also contemplated.

The suturing device 200 further includes suture guides 240 on the first guide member 208. The suture guides 240 may be separate components mounted on or attached to the first guide member 208 or may be integrally formed with the first guide member 208. In the embodiment shown in FIGS. 7-8, each of the suture guides 240 is a cylindrical tube aligned in a direction generally transverse to the first guide member 108. Those skilled in the art will appreciate that any similar structure configured to direct a suture needle 242 (FIG. 10) in a desired direction may be used as one or more of the suture guides 240 instead of, or in addition to, the cylindrical tubes. For example, each of the suture guides 240 may alternatively be a hook member (not shown) with an eyelet through which the suture needle 242 is inserted. In another embodiment, each of the suture guides 240 may simply be a perforation or opening (not shown) formed through a portion of the first guide member 208. The number of and spacing between the suture guides 240 may be varied depending on the size and shape of tissue being sutured.

Because the suture guides 240 are coupled to the first guide member 208, their position relative to the tissue being sutured may be adjusted by moving the first portion 212 of the first guide member 208 relative to the second portion 216. More specifically, as with the first guide member 108 (FIGS. 2-6), the first guide member 208 defines an arcuate profile between the arm 220 and the arm 228 when the first collar 124 and second collar 130 are received on the shaft 102. The shape of this arcuate profile (and thus the position of the suture guides 240) may be adjusted by rotating the shaft 102 relative to the first guide member 208. This rotation causes the first collar 124 to move along the threaded portion 140 in an axial direction relative to the second collar 130. In turn, the first guide member 208 flexes outwardly or inwardly (depending on the direction of relative movement in the axial direction) until the suture guides 240 confront the desired tissue to be sutured.

Advantageously, a portion of the tissue to be sutured may be gripped or held between the first guide member 208 and the second guide member 210, with the second guide member 210 flexing along with the first guide member 208 so as to have the same arcuate profile. In some embodiments, at least one of the first portion 112 or the second portion 116 of the first guide member 108 may be coupled to a different collar (not shown) than the corresponding first portion 114 or the second portion 118 of the second guide member 110. These different collar(s) may be rotated relative to the first collar 124 and/or second collar 130 to adjust the spacing between the first guide member 108 and second guide member 110 depending upon the size of the tissue to be gripped therebetween. Such gripping arrangements help stabilize the tissue when the suture needle 242 is advanced through the suture guides 240. Nevertheless, although the second guide member 210 is shown in FIGS. 7-8, the suturing device 200 may alternatively be provided with only the first guide member 208.

In addition to the suture guides 240, the suturing device 200 may further include a first ring member 244 and a second ring member 246 coupled to the shaft 102 at spaced apart locations. In the exemplary embodiment shown in FIGS. 7-8, the first ring member 244 is coupled to the distal end 132 of the shaft 102 and the second ring member 246 is coupled to the first section 136 of shaft 102 between the second collar 130 and the second section 138. The first ring member 244 and the second ring member 246 may each be a cylindrical tube aligned generally orthogonal to a longitudinal axis 250 of the shaft 102.

An external needle guide 252 (FIG. 9) is configured to be inserted through at least one of the first ring member 244 and second ring member 246 and received by the other one of the first ring member 244 and second ring member 246. In one embodiment (an example of which is described in greater detail below with reference to FIG. 17), the external needle guide 252 has a generally straight configuration, but is constructed from a flexible material so that it may be directed outwardly from the second ring member 246, around the tissue to be sutured, and back toward the shaft 102 until a distal end portion 254 is received in the first ring member 244. In another embodiment, the external needle guide 252 is constructed from a shape-memory material so that it assumes the necessary curvature to extend around the tissue to be sutured between the first ring member 244 and second ring member 246 once the suturing device 200 is inserted into a patient's body. For example, the external needle guide 252 may have a generally straight configuration at room temperature, but assume a curved configuration at approximately 37° C. (i.e., body temperature). The shape-memory material in such an embodiment is a thermoresponsive material. However, it will be appreciated that any shape memory alloy or polymer may be used. The external needle guide may also be constructed from piezoelectric materials or other "smart" materials that change shape in response to a stimulus.

As shown in FIGS. 9-12, the external needle guide 252 may be a cannulated tube having a substantially C-shaped cross-section. Such a cross-section includes a slot 256 along at least a portion of the length of an outer body 258 that surrounds an inner channel 260 of the external needle guide 252. A suture thread 262 may be preloaded into the inner channel 260 so that a first end portion 264 of the suture thread 262 freely extends beyond the distal end portion 254 of the external needle guide 252 and a second end portion 266 freely extends beyond a proximal end portion 268 of the external needle guide 252. The slot 256 includes openings 270 each configured to accommodate the suture needle 242 when the suture guides direct the suture needle 242 through tissue to the external needle guide 252, as will be described below. In one embodiment, the openings 270 are each defined by a semi-circular notch 272 formed into a first edge 274 of the slot 256 and an elongated notch 276 formed into a second edge 278 of the slot 256 opposite the semi-circular notch 272. The elongated notches 276 each include an arcuate segment 280 and a ramp 282 extending from the arcuate segment 280 to the second edge 278, the purpose of which will be described below as well.

The external needle guide 252 also includes openings 288 on the outer body 258 opposite the openings 270. Each of the openings 270 and openings 288 may be aligned with a corresponding one of the suture guides 240 when the external needle guide 252 is properly positioned relative to the shaft 102. Thus, when the suture needle 242 is directed by one of the suture guides 240 through tissue and toward the external needle guide 252, the suture needle 242 may be advanced through a corresponding one of the openings 270 and into the inner channel 260 until a tip 290 of the suture needle 242 extends through a corresponding one of the openings 288.

Figure 12:
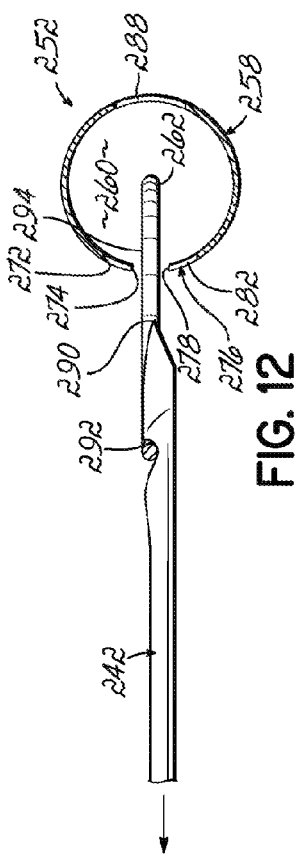
Figure 13:
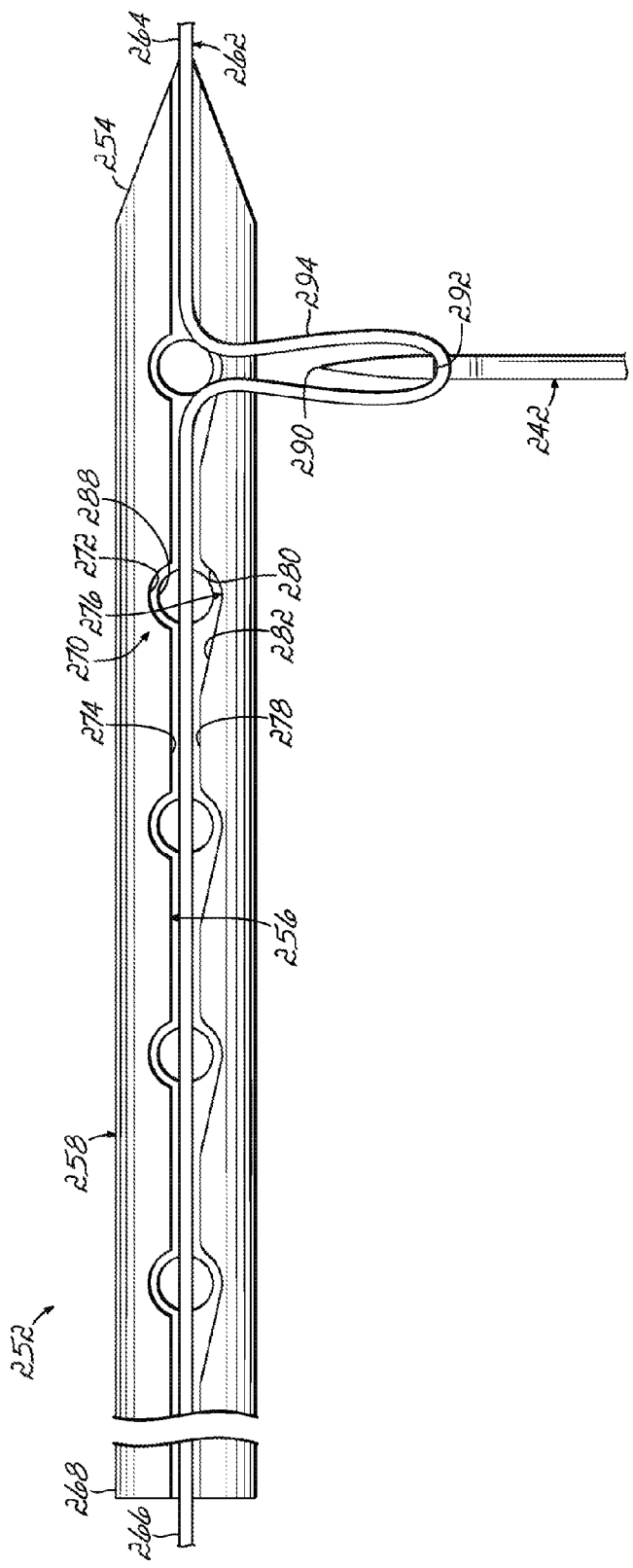
FIG. 13 is a side elevational view similar to FIG. 9 showing the suture thread pulled from the external needle guide.

A hook 292 configured to catch or grab onto the suture thread 262 is provided on the suture needle 242 at a location spaced from the tip 290. Once the suture needle 242 is advanced far enough through the inner channel 260 for the hook 292 to catch the suture thread 262, the suture needle 242 may be retracted from the external needle guide 252 and back through the tissue and associated suture guide 240. The hook 292 pulls the suture thread 262 out of the inner channel 260 through one of the openings 270 to form a suture loop 294, as shown in FIGS. 12 and 13. Because of this retraction, the first end portion 264 and/or second end portion 266 of the suture thread 262 are pulled through the inner channel 260 in a direction toward the suture loop 294. The tissue surrounding the suture loop 294 helps prevent the suture thread 262 from being pulled out of the inner channel 260 at locations spaced away from the corresponding one of the openings 270 through which the suture loop 294 extends. Additionally, the first end portion 264 and second end portion 266 each have a length configured to provide an adequate supply of the suture thread 262 for forming multiple loops.

A method of cutting and suturing tissue using both the cutting device 100 and suturing device 200 will now be described in greater detail. More specifically, a method of using the cutting device 100 and suturing device 200 to replace the damaged portion 44 (FIG. 1) of the medial meniscus 10 (which includes the tear 40) with the implant 46 will now be described. Although the method focuses on the cutting device 100 and the suturing device 200, certain aspects may be used with other meniscus repair and/or replacement procedures not requiring these specific tools. Additionally, although the methods will be described with reference to the medial meniscus 10, the methods may equally apply to the treatment of tears in the lateral meniscus 8.

Figure 14:
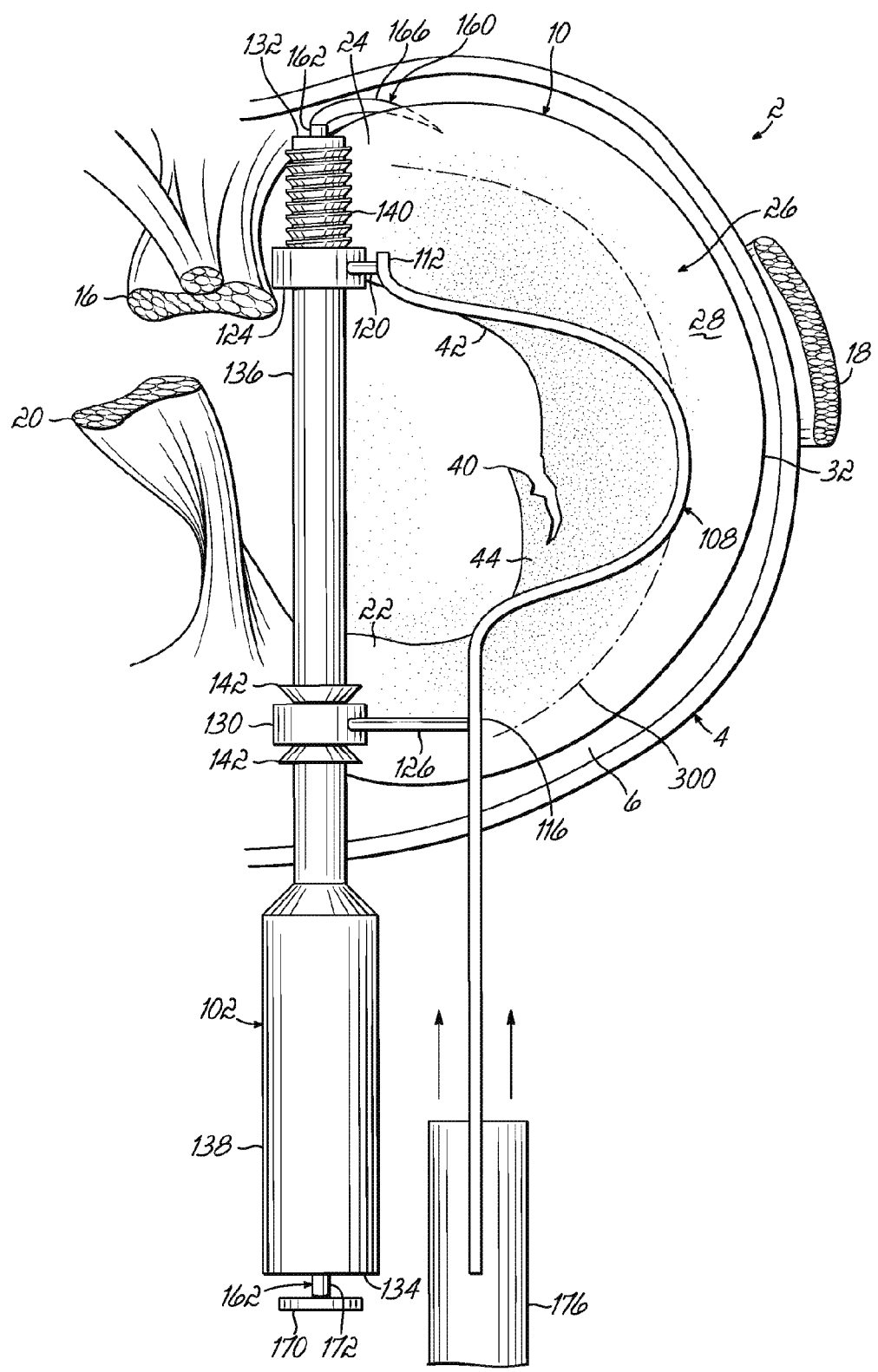
FIGS. 14-21 sequentially illustrate a method of replacing a portion of the lateral meniscus of FIG. 1 using the cutting device of FIG. 2 and the suturing device of FIG. 7.

Once a physician has discovered the presence of the tear 40, one of the first steps involved in treatment is to evaluate the location and geometry of the tear 40. This information may be used by the physician to determine whether the tear 40 can be repaired or whether the damaged portion 44 including the tear 40 must be replaced. As explained above, tears not confined to the outer one-third, or "red zone," of a meniscus are not typically repaired because of the lack of blood supply to other regions of the meniscus. FIG. 14 illustrates the tear 40 extending from the inner edge 42 of the medial meniscus 10. Because the tear 40 is located in the inner one-third, or "white zone," of the medial meniscus 10, a replacement procedure would likely be the most effective method of treatment.

Advantageously, the replacement procedure described below may be performed using arthroscopic techniques. In other words, in a manner not shown herein, a camera attached to a fiber optic light source is first inserted into the knee joint 2 through a small incision (approximately ⅛ inch to ¼ inch long). Fluid is then added to distend the knee joint 2 so that the structures within the knee joint 2 captured by the camera may be visualized on a monitor. Next, another small incision is made and the cutting device 100 is inserted into the knee joint 2 through a portal or delivery cannula. The cutting procedure described below with reference to the cutting device 100 and the suturing procedure described below with reference to the suturing device 200 (which may be inserted into the knee joint 2 in a similar manner as the cutting device 100) are both performed using the visualization provided by the arthroscopic camera. As a result, large incisions that can lead to increased recovery times and discomfort for a patient are not required. Nevertheless, the cutting device 100 and suturing device 200 may b used in connection with a mini-arthrotomy or any other surgical techniques that require larger incisions if desired.

The components of the cutting device 100 may be inserted into the knee joint 2 as assembled or individually for subsequent assembly within the knee joint 2. For example, the rod 162 and hook 166 of the attachment member 160 may first be inserted through an incision (not shown) on the anterior side of the knee joint 2. The rod 162 may then be advanced through the knee joint 2 so that the hook 166 can anchor into the posterior horn 24, as shown in FIG. 14. Next, the shaft 102, which may or may not be pre-assembled with the cutting guide 104, is inserted through the incision and over the rod 162. Finally, the handle 170 may be secured to the rod 162 to retain the shaft 102 on the attachment member 160.

The shaft 102 and cutting guide 104 are inserted into the knee joint 2 so that at least a portion of the medial meniscus 10 is positioned between the first guide member 108 and second guide member 110. For example, the first guide member 108 may be positioned proximate the superior surface 28 and the second guide member 110 may be positioned proximate the inferior surface 30 (FIGS. 22-24) of the medial meniscus 10. Such an arrangement prevents the cutting guide 104 from moving relative to the shaft 102 when a surgeon rotates the shaft 102 to adjust the position of the first collar 124 relative to the second collar 130. This rotation causes the first guide member 108 and second guide member 110 to change the profile of the arcuate cutting path defined for the blade 106, as described above.

The adjustable nature of the arcuate cutting path not only enables the cutting device 100 to accommodate a wide variety of tear shapes and sizes, but also allows the cutting plane to be set at an optimal location for attachment of the implant 46 (FIG. 1 A). In particular, the arcuate cutting path may be adjusted until at least a portion of the path extends to an area in the intermediate or red zone of the medial meniscus 10. The boundary between the red zone and intermediate zone of the medial meniscus 10 is schematically shown by the line 300 in FIG. 14. Additionally, for reasons described in greater detail below, a scale or similar markings (not shown) may be provided on the shaft 102 so that a surgeon may reference the position of the first collar 124 relative to the second collar 130 when a desired profile of the arcuate cutting path is obtained.

Once the cutting device 100 is properly positioned and the arcuate cutting path is adjusted to the desired profile, the surgeon advances the blade 106 along the first guide member 108 and second guide member 110. The blade 106 may be advanced using the wire 174 (together with the protective insulation 176) and/or or other miniature surgical tools designed for arthroscopic procedures. As the blade 106 travels along the arcuate cutting path, the first sharp edge 154 and second sharp edge 156 cut through the medial meniscus 10. The wire 174 may be used to heat the blade 106 to facilitate this cutting operation, as discussed above.

Figure 15:
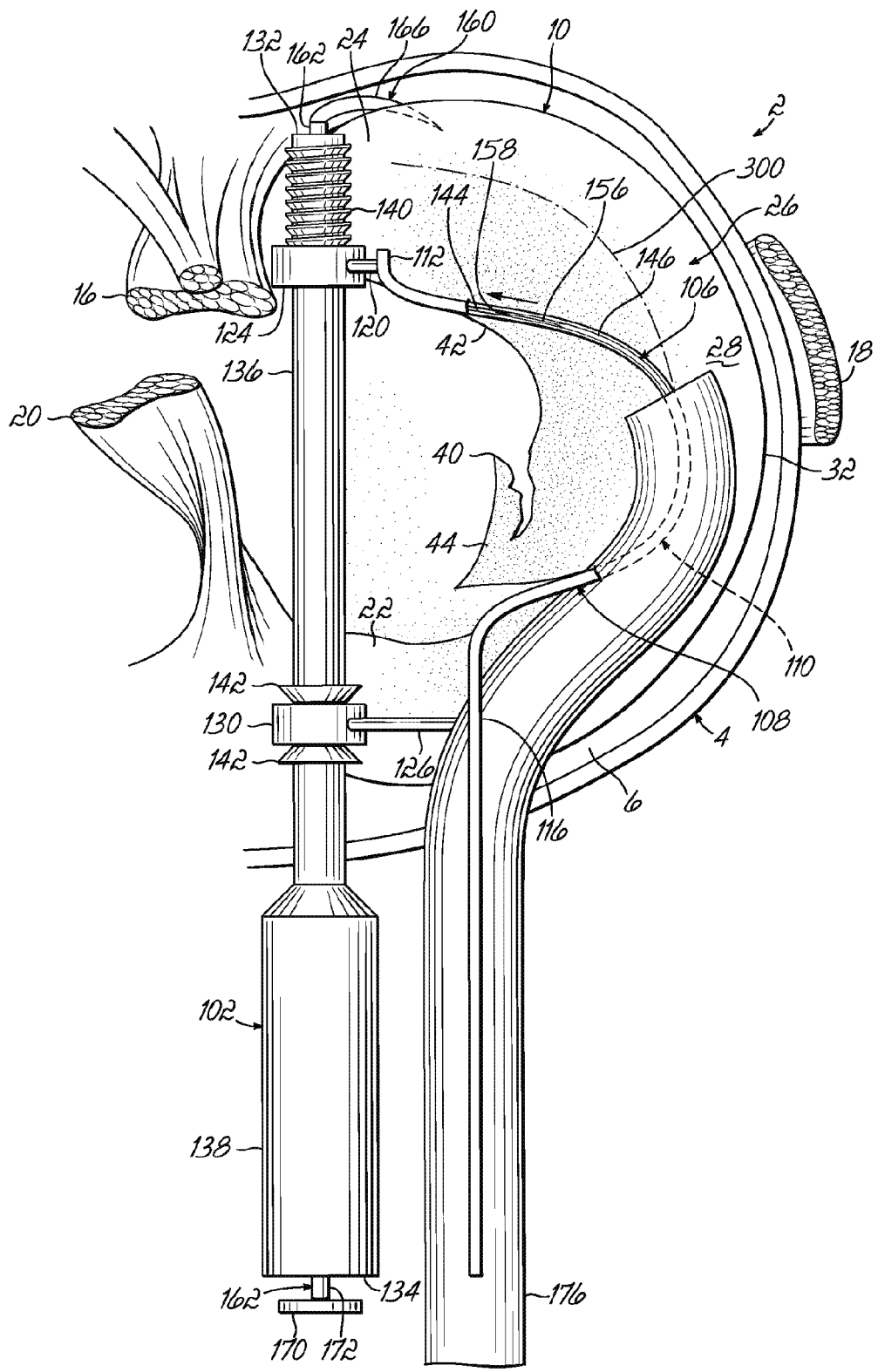
Figure 16:
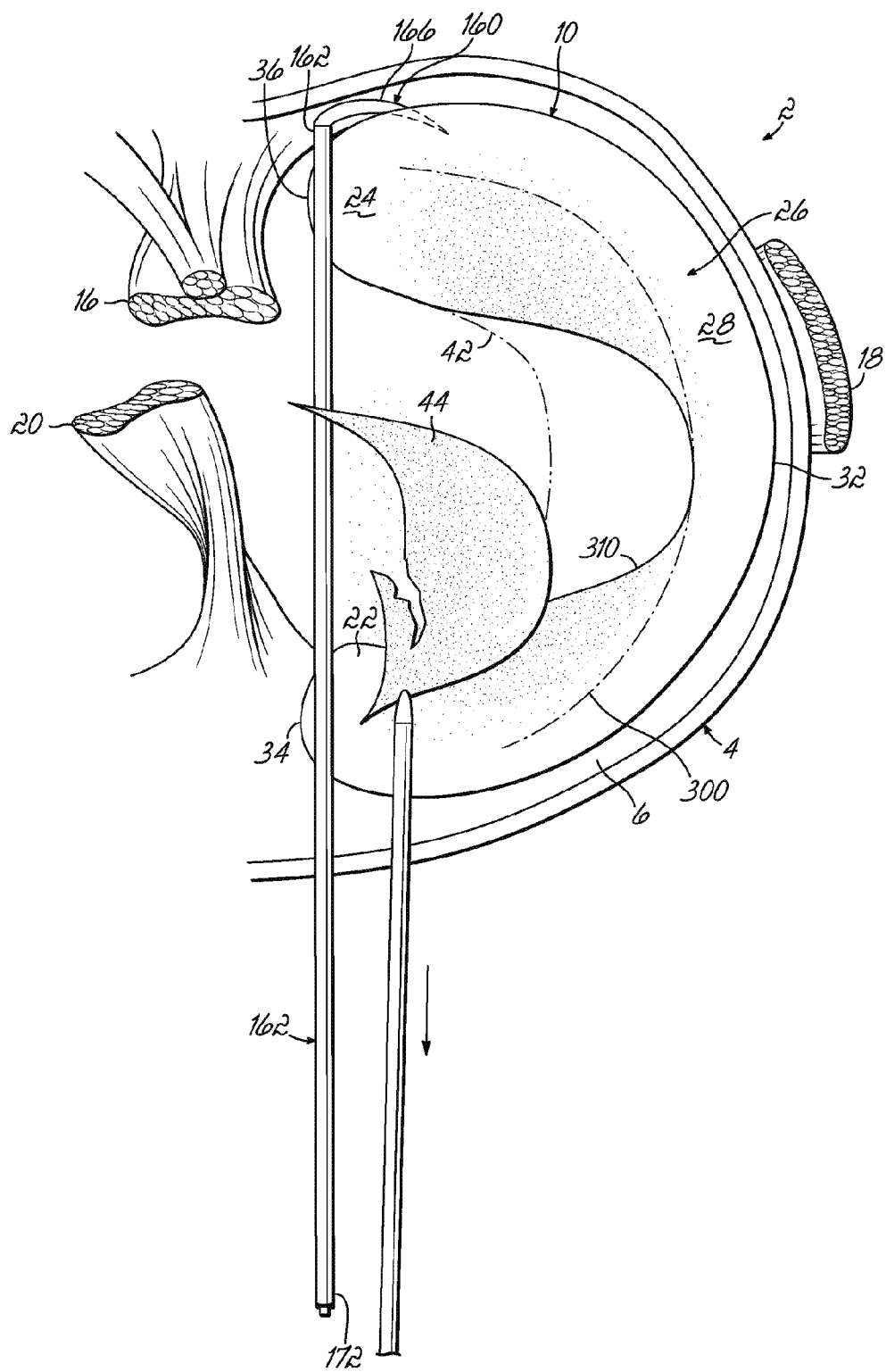

FIG. 15 illustrates the blade 106 after it has been advanced a certain distance along the arcuate cutting path. By the time the blade 106 approaches the first portion 112 of the first guide member 108 and the first portion 114 of the second guide member 110, the damaged portion 44 is completely severed from the remainder of the medial meniscus 10. The damaged portion 44 may then be removed from the knee joint 2 using forceps or any other suitable surgical instrument. As shown in FIG. 16, the shaft 102 and cutting guide 104 may also be removed from the knee joint 2 before or after removing the damaged portion 44. For example, the handle 170 of the attachment member 160 may be uncoupled from the rod 162, which would then allow a surgeon to remove the shaft 102 and cutting guide 104 along the rod 162. Such a procedure results in the rod 162 remaining within the knee joint 2 with the hook 166 secured to the posterior horn 24.

Before delivering the implant 46 to the knee joint 2 to replace the damaged portion 44, several steps may be taken to optimize the implant 46 for attachment to the medial meniscus 10. For example, the implant 46 may be cut to match the shape of an exposed surface 310 on the remainder of the medial meniscus 10 that extends along the cutting plane of the blade 106. This may be accomplished using the cutting device 100 after it has been removed from the knee joint 2. Specifically, the shaft 102 and cutting guide 104 may be removed from the knee joint 2 without adjusting the position of the first collar 124 relative to the second collar 130. Although the first guide member 108 and second guide member 110 may flex inwardly to fit through a portal or cannula, they are able to flex outwardly back to the same profile used to cut the damaged portion 44 once removed from the knee joint 2. The implant 46 may then be positioned relative to the cutting guide 104 and trimmed by the blade 106 so that an attachment surface 312 (FIG. 1A) of the implant 46 has a shape that generally corresponds to the exposed surface 310 of the medial meniscus 10.

In embodiments in which a scale or similar markings are provided on the shaft 102, the position of the first collar 124 relative to the second collar 130 may be adjusted after being referenced by the surgeon before the cutting device 100 is removed from the knee joint 2. As a result, the arcuate profile of the first guide member 108 and second guide member 110 may then be reduced to facilitate removal of the cutting device 100 through a portal or cannula. If desired, the cutting guide 104 may even be removed completely from the shaft 102 within the knee joint 2 so that the components are removed from the knee joint 2 separately. The surgeon need not worry about maintaining the position of the first collar 124 relative to the second collar 130 because he or she knows what position or arrangement on the scale corresponds to the arcuate cutting path used to cut the damaged portion 44 of the medial meniscus 10. Once the cutting guide 104 and shaft 102 are removed from the knee joint 2, the surgeon may reassemble the cutting device 100 and adjust the position of the first collar 124 and the second collar 130 back to the referenced position on the scale corresponding to the arcuate cutting path.

In some situations, several different allograft or xenograft implants may be available. The available implants may be compared to the damaged portion 44, the cutting guide 104, and/or measurements of the medial meniscus 10 taken with other tools (not shown) to determine which implants are a suitable size before trimming them with the cutting guide 104.

Additionally, the ability to visualize the exposed surface 310 of the medial meniscus 10 may be used help optimize the implant 46 for attachment. For example, after removing the damaged portion 44, a surgeon may take an image of the exposed surface 310. The exposed surface 310 includes some vascular structure 314 (FIGS. 22-24) because at least a portion of the exposed surface 310 extends to the outer one-third, or red zone, of the medial meniscus 10. The vascular structure seen in the image of the exposed surface 310 is then compared to the vascular structure 316 (FIGS. 22-24) along the attachment surface 312 of each implant that has been shaped for attachment. Once the implant with the closest vascular structure to that of the exposed surface 310 is determined, that particular implant is selected for attachment to the remainder of the medial meniscus 10. The implant 46 represents the implant selected using this procedure.

Selecting the implant with the closest vascular structure to the exposed surface 310 helps promote the regeneration of tissue. Specifically, by selecting the implant with the closest vascular structure, the amount of blood flow between the implant and the remainder of the medial meniscus 10 is likely to be increased. The cells and nutrients delivered by the blood help form new tissue to join together the implant 46 and the medial meniscus 10.

Figure 17:
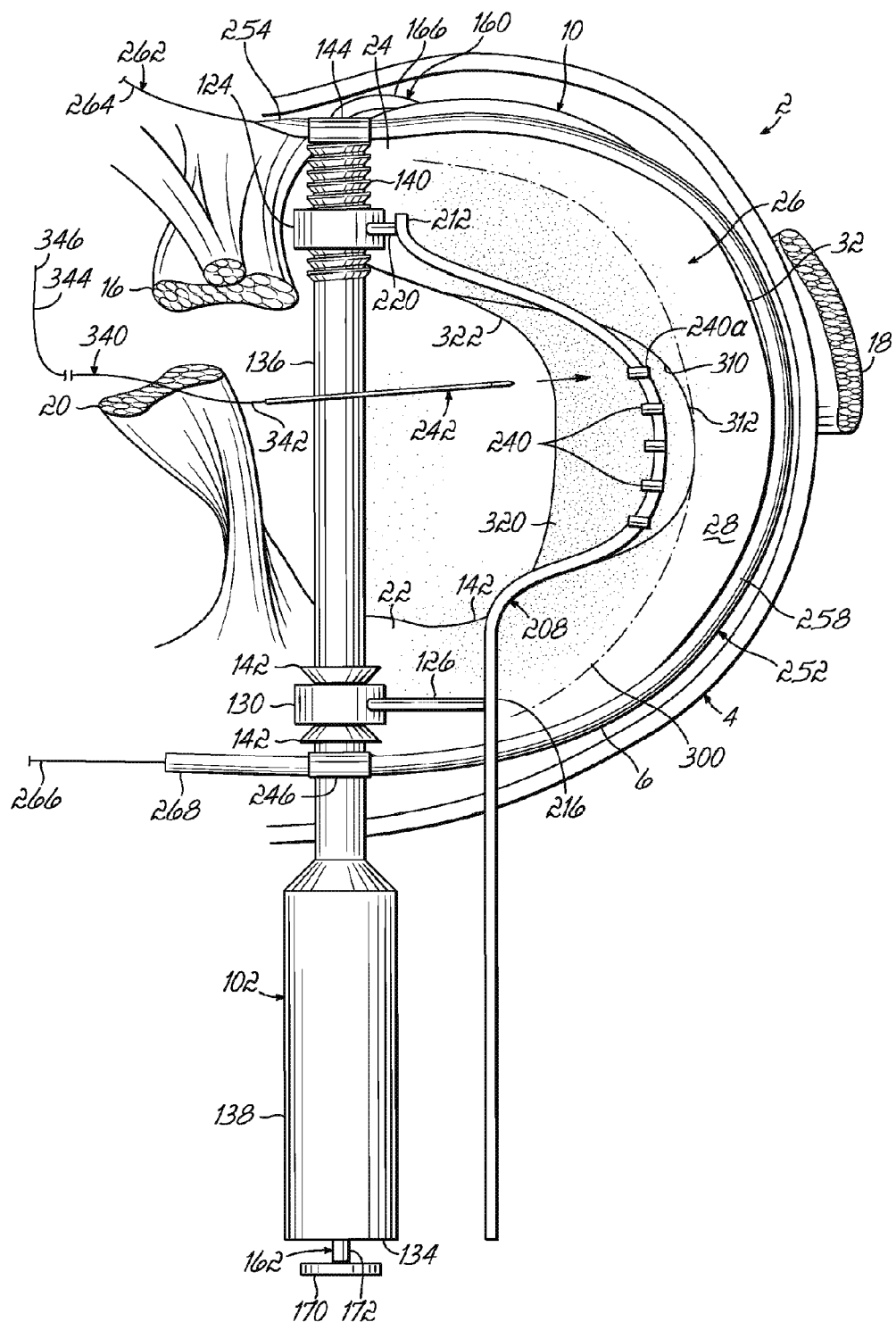
Figure 18:
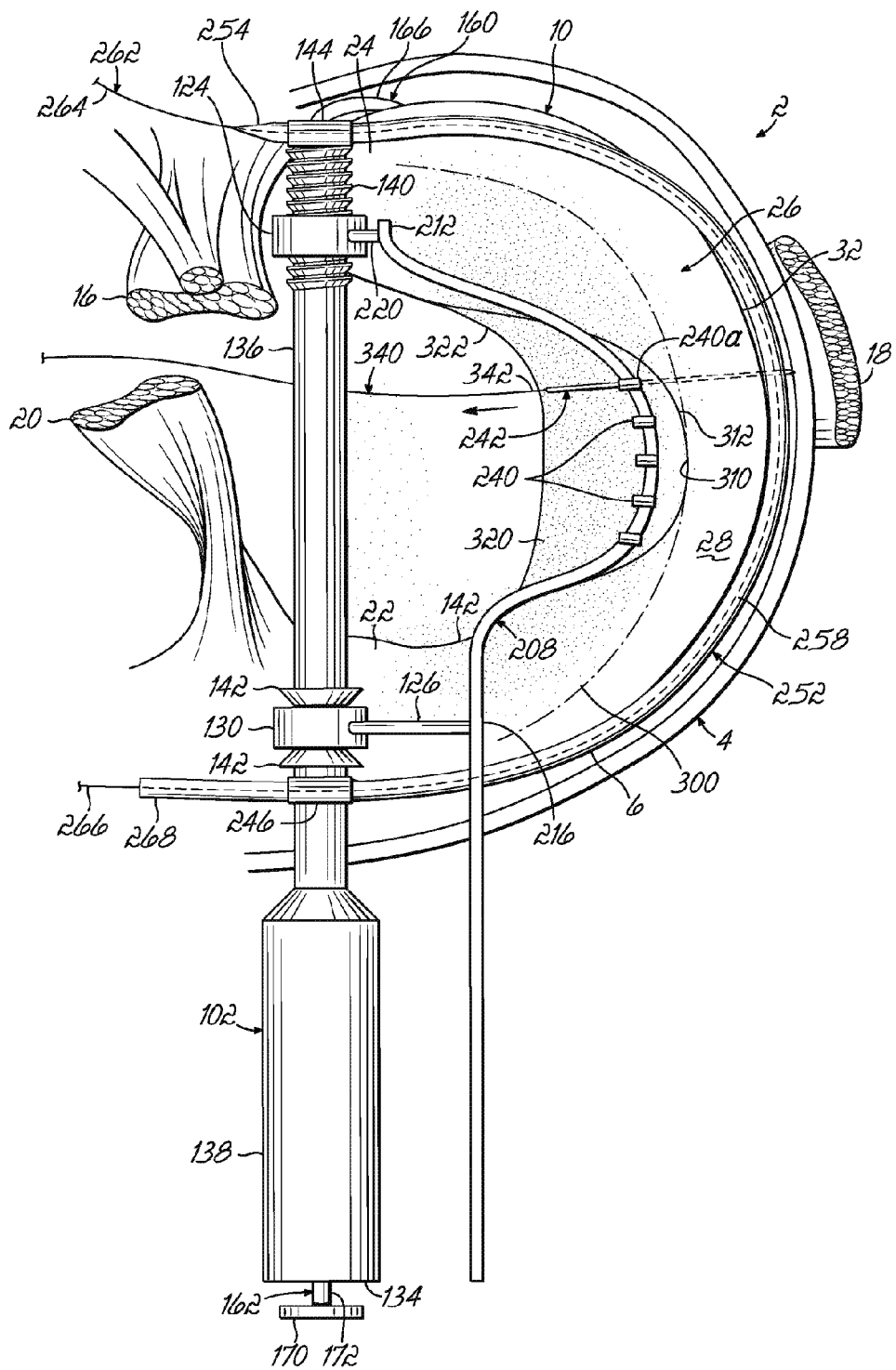

Referring now to FIG. 17, both the suturing device 200 and implant 46 are shown within the knee joint 2. The suturing device 200 may be inserted into the knee joint 2 in the same manner as the cutting device 100. Indeed, once the first guide member 208 and second guide member 210 are coupled to the shaft 102 (via the first collar 124 and second collar 130), the shaft 102 may be inserted over the attachment member 160, which may remain within the knee joint 2. The handle 170 is then once again coupled to the rod 162 to retain the shaft 102 on the attachment member 160. However, it will be appreciated that the cutting device 100 and suturing device 200 may alternatively include separate attachment members (not shown) such that there is complete removal of the cutting device 100 before insertion of the suturing device 200. Additionally, the first guide member 208 and second guide member 210 may alternatively be coupled to the shaft 102 after the shaft 102 is inserted into the knee joint 2 and over the rod 162.

The implant 46 may be delivered within the knee joint 2 before, during, or after the insertion of the suturing device 200. For example, in one embodiment, the implant 46 may be gripped between the first guide member 208 and second guide member 210 while being inserted into the knee joint 2 along with these components. In another embodiment, the implant 46 is delivered to its approximate position relative to the medial meniscus 10 prior to inserting the suturing device 200. Once the suturing device 200 is inserted, the implant 46 is then gripped between the first guide member 208 and second guide member 210 and moved into its desired suturing position with the attachment surface 312 confronting the exposed surface 310.

As can be seen in FIG. 17, the first guide member 208 may be positioned against the superior surface 28 of the medial meniscus 10 and against an upper surface 320 of the implant 46 that generally corresponds to the superior surface 28 when the implant 46 is properly positioned relative to the medial meniscus 10. The second guide member 210 is not shown because it is positioned between the inferior surface 30 of the medial meniscus 10 and the joint surface 6 of the tibia 4. By rotating the shaft 102, the surgeon is able to move the first collar 124 relative to the second collar 130 to adjust the arcuate profile defined by the first guide member 208 and the second guide member 210, as discussed above. The position of the first collar 124 is adjusted relative to the second collar 130 until the first guide member 208 extends across the upper surface 320 between at least a portion of the attachment surface 312 and an inner edge 322 of the implant 46. Because the upper surface 320 of the implant 46 is inclined from the inner edge 322 to the attachment surface 312, such an arrangement results in the suture guides 240 being configured to direct the suture needle 242 along corresponding paths extending through both the implant 46 and the medial meniscus 10.

FIG. 17 also illustrates the external needle guide 252 positioned within the knee joint 2. The external needle guide 252 may be inserted through the second ring member 246 and over a portion of the anterior horn 22 until it reaches the lateral surface 32 of the medial meniscus 10. As described above, the external needle guide 252 may be constructed from a flexible material. This would allow the surgeon to bend or flex the external needle guide 252 around the medial meniscus 10 along the lateral surface 32 until the distal end portion 254 extends over a portion of the posterior horn 24 and into or through the first ring member 244. If constructed from a shape-memory material, the external needle guide 252 may be configured to assume a curvature that generally corresponds to the shape of the lateral surface 32 after the external needle guide 252 is inserted into the knee joint 2. A surgeon would then "fish" or direct the external needle guide 252 around the lateral surface 32 until the first ring member 244 receives the distal end portion 254.

The distal end portion 254 may be advanced through the first ring member 244 until the openings 270 in the external needle guide 252 are approximately aligned with the suture guides 240. Because the proximal end portion 268 of the external needle guide 252 does not extend through the second ring member 246, the external needle guide 252 is maintained in close contact with the lateral surface 32 of the medial meniscus 10. Once the first guide member 208 is properly positioned on the superior surface 28 and the upper surface 320 of the medial meniscus 10, the suture needle 242 may be introduced into and manipulated within the knee joint 2 using arthroscopic techniques.

FIGS. 18 and 22-24 illustrate the suture needle 242 being inserted through a first one of the suture guides 240 to initiate the suturing process. More specifically, a surgeon inserts the suture needle 242 through the first suture guide 240a, which then directs the suture needle 242 in a lateral direction through both the implant 46 and the medial meniscus 10. The tip 290 of the suture needle 242 eventually extends through one of the openings 270 and one of the openings 288 in the external needle guide 252 aligned with the first suture guide 240a so that the hook 292 catches onto or grabs the suture thread 262 within the inner channel 260, as described above with reference to FIGS. 9-12. Once the hook 292 engages the suture thread 262, the surgeon retracts the suture needle 242 back through the medial meniscus 10, through the implant 46, and out the first suture guide 240a. The first guide member 208 and second guide member 210 help stabilize the implant 46 to maintain the attachment surface 312 proximate the exposed surface 310 during this retraction. Additionally, one or both of the first end portion 264 and second end portion 266 of the suture thread 262 are drawn toward the inner channel 260 of the external needle guide 252 to accommodate suture thread 262 being pulled back through the medial meniscus 10 and implant 46.

Figure 19:
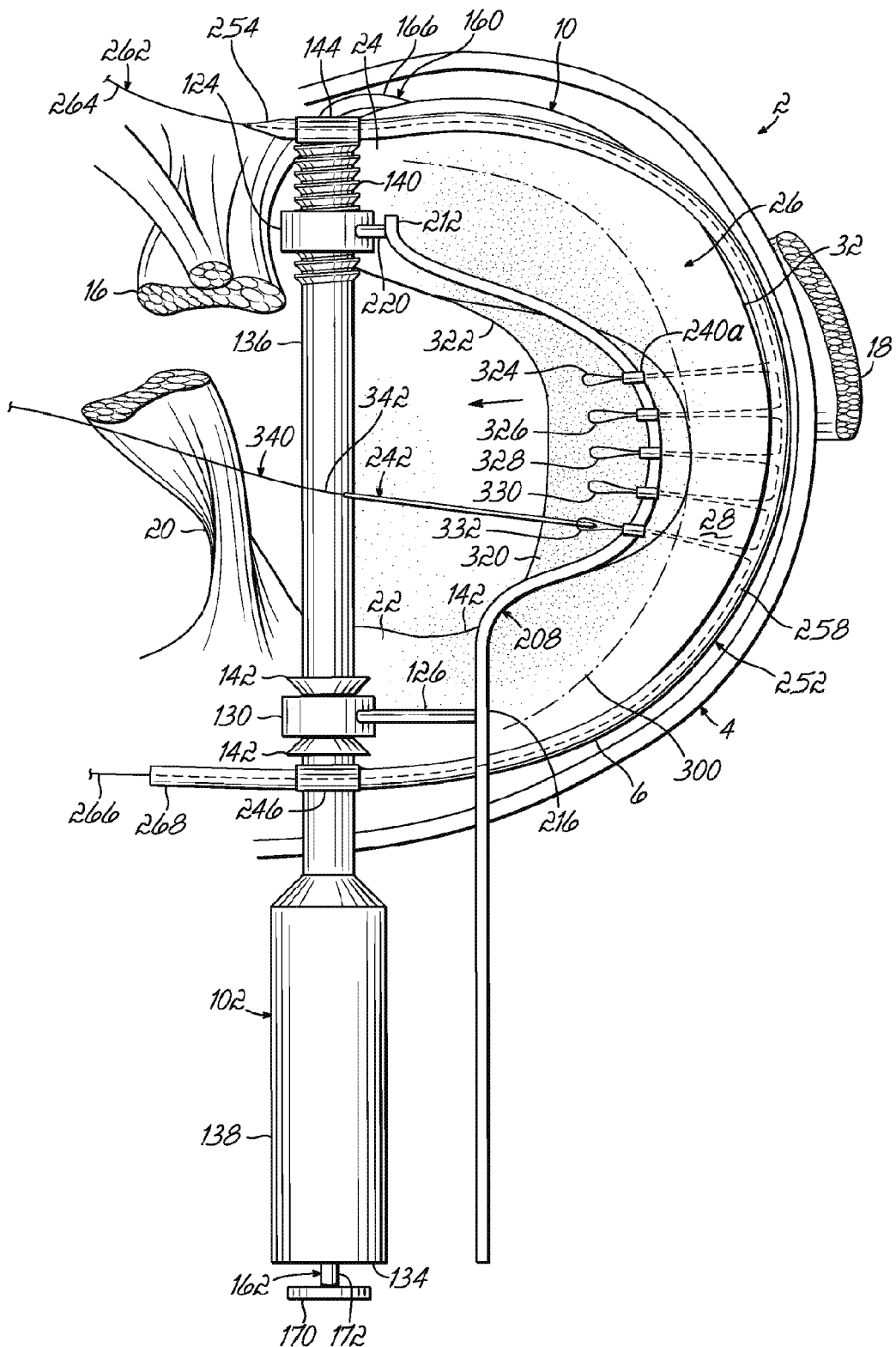

After the tip 290 of the suture needle 242 has been retracted past the first suture guide 240a, the hook 292 may be disengaged from the suture thread 262. The result is a first suture loop 324 (FIG. 19) of the suture thread 262 extending from the upper surface 320 of the implant 46. As shown in FIG. 19, the surgeon may then proceed to insert and retract the suture needle 242 through the remainder of the suture guides 240 to form additional suture loops 326, 328, 330, and 332 extending from the upper surface 320. The first end portion 264 and second end portion 266 of the suture thread 262 are long enough to provide an adequate supply of the suture thread 262 for this purpose, as mentioned above.

Once the last suture loop 332 has been formed, the suturing device 200 may be completely removed from the knee joint 2. The removal process is initiated by first advancing the external needle guide 252 all the way around the lateral surface 32 until the proximal end portion 268 extends through the first ring member 244. A portal (not shown) may be created on the posterior side of the knee joint 2 to accommodate the distal end portion 254 and allow for removal of the external needle guide 252 as it is advanced in this manner. Additionally, because the suture loops 324, 326, 328, 330, and 332 extend through the slot 256 formed in the outer body 258, the external needle guide 252 may be advanced in this manner without removing the suture thread 262 from the knee joint 2.

For example, referring back to FIG. 13 and the suture loop 294, the slot 256 allows the external needle guide 252 to be advanced past the suture loop 294. The ramp 282 of the elongated notch 276 helps prevent the suture loop 294 from catching on the second edge 278 of the slot 256 as the external needle guide 252 is advanced. In particular, the ramp 282 provides a gradual transition from the arcuate segment 280 to the second edge 278 to help direct the portion of the suture loop 294 proximate the outer body 258 into the slot 256 whenever one of the openings 270 pass over the suture loop 294. Although only the elongated notches 276 are shown as having the ramp 282, the semi-circular notches 272 may alternatively be provided with a similar configuration as the elongated notches 276.

With the external needle guide 252 removed from the knee joint 2, the remaining components of the suturing device 200 may then be removed. The components may be removed as assembled or may be separated within the knee joint 2 and removed individually. For example, in one embodiment, a surgeon simply disengages the hook 166 from the posterior horn 24 and then removes the entire suturing device 200 from the knee joint 2 through the same portal through which it was inserted. The suture guides 240 each slide over the corresponding suture loop 324, 326, 328, 330, or 332 during this removal because the suture loops 324, 326, 328, 330, and 332 are freely received in the suture guides 240. However, if desired, the shaft 102 may be rotated prior to removal to move the first collar 124 along the shaft 102 in a direction away from the second collar 130. This movement results in the first guide member 208 flexing toward the shaft 102 (i.e., moving toward a straight configuration) and the suture guides 240 moving over the suture loops 324, 326, 328, 330, and 332. Once the suture loops 324, 326, 328, 330, and 332 no longer extend through the suture guides 240, the suturing device 200 is removed from the knee joint 2.

Figure 20:
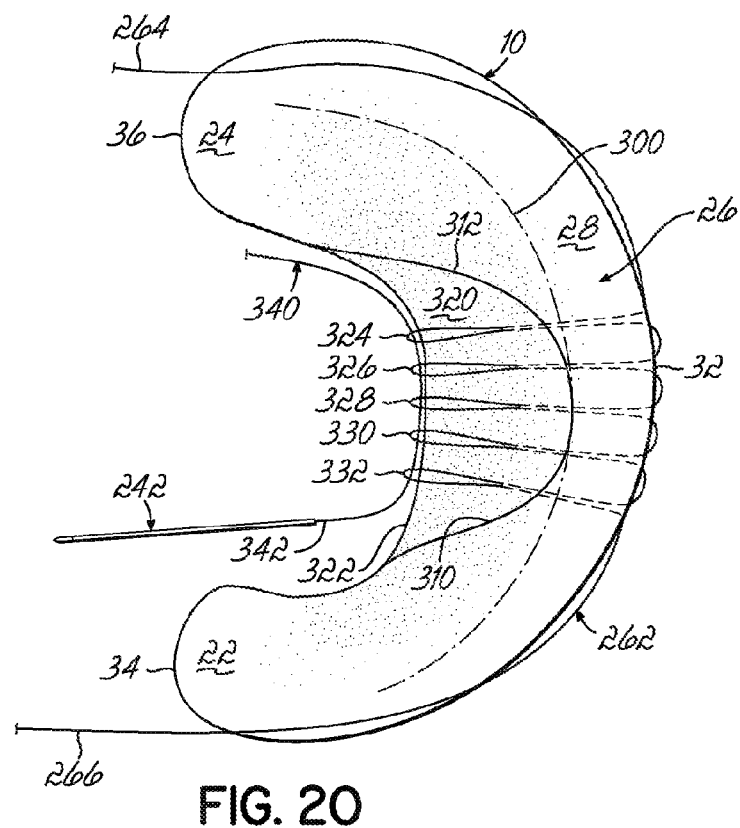
Figure 21:
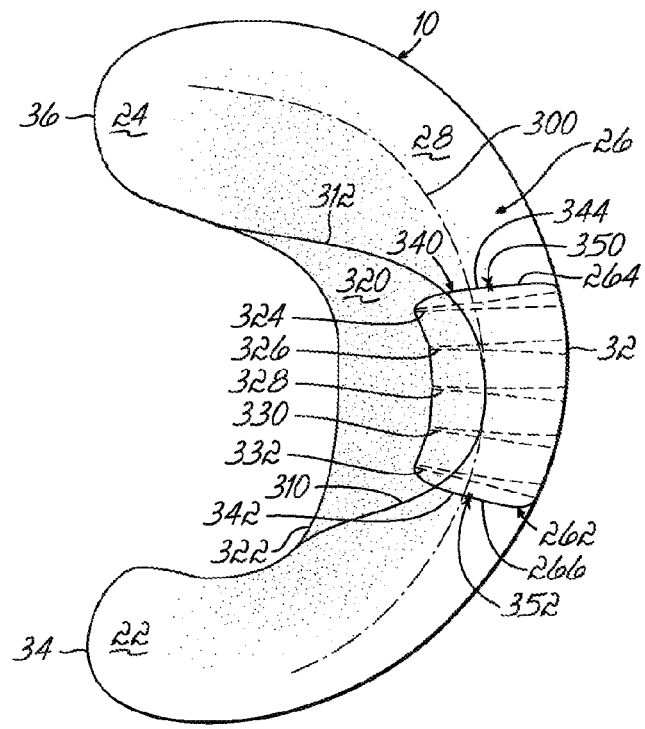

FIG. 20 illustrates the medial meniscus 10 and implant 46 after the external needle guide 252 and remainder of the suturing device 200 have been removed from the patient's body (the other structures associated with the knee joint 2 are not shown for the purposes of clarity). A suture thread 340 is coupled to the suture needle 242, which is inserted through each of the suture loops 324, 326, 328, 330, and 332. The suture thread 340 is long enough so that a first end portion 342 proximate the suture needle 242 extends through the suture loops 324, 326, 328, 330, and 332, while a second end portion 344 proximate a free end 346 does not.

Once the suture needle 242 extends through the suture loops 324, 326, 328, 330, and 332, a surgeon may pull the first end portion 264 and second end portion 266 relative to each other to place the suture thread 262 in tension. This tensioning tends to pull the suture loops 324, 326, 328, 330, and 332 back toward the lateral surface 32 of the medial meniscus 10. The suture loops 324, 326, 328, 330, and 332 are pulled back through the implant 46 until they reach the upper surface 320, at which point the suture thread 340 prevents further retraction. As a result, the tensioning then causes the suture loops 324, 326, 328, 330, and 332 to pull the implant 46 tightly against the medial meniscus 10.

The first end portion 342 of the suture thread 340 may be cut or uncoupled from the suture needle 242 before or after the suture thread 262 is tensioned. In either case, once the implant 46 has been pulled firmly against the medial meniscus 10 by the suture loops 324, 326, 328, 330, and 332, the first end portion 264 of the suture thread 262 may be tied to the second end portion 344 of the suture thread 340 to form a knot 350. Likewise, the second end portion 266 of the suture thread 262 may be tied to the first end portion 342 of the suture thread 340 to form a knot 352. Such a suturing arrangement secures the implant 46 to the medial meniscus 10 with the attachment surface 312 in apposition with the exposed surface 310.

It will be appreciated that the same type of suturing arrangement may also be achieved using a single suture thread and single knot. For example, after the suture loops 324, 326, 328, 300, and 332 have been formed and the suturing device 200 has been removed from the knee joint 2, the suture needle 242 may be coupled to the first end portion 264 or second end portion 266 of the suture thread 262. If coupled the first end portion 264, the suture needle is then directed through the suture loops 324, 326, 328, 330, and 332 to position the first end portion 264 near the second end portion 266. The suture needle 242 is then uncoupled from the first end portion 264 and removed from the knee joint 2. After pulling the first end portion 264 and second end portion 266 to tension the suture thread 262 and firmly secure the implant 46 to the medial meniscus 10, the first end portion 264 may be tied to the second end portion 266 to form a single knot (not shown) on the superior surface 28.

Using the suturing device 200 to complete the replacement procedure offers several advantages. For example, in existing systems, the surgeon must estimate where and how to insert suture thread through a meniscus to securely attach an implant. The ability to form multiple suture loops is limited due to the difficulty associated with maneuvering the suture needle around the geometry of the meniscus. In contrast, the suturing device 200 provides the surgeon with some guidance on where to insert a suture needle. Because of manner in which the suture guides 240 facilitate the suturing process, the number and spacing of the suture guides 240 may allow for the formation of a relatively large number of suture loops through the tissue that would otherwise not be possible. The combination of the first guide member 208, suture guides 240, and external needle guide 252 also provide the surgeon with a predetermined pattern for the suture to be formed. In summary, the suturing device 200 allows for easier and more precise attachment of an implant to a meniscus or other tissue.

Although a method of replacing a portion of the medial meniscus 10 is described above, those skilled in the art will appreciate that the suturing device 200 may also be used to repair a torn meniscus when appropriate. For example, after evaluating the location and geometry of a tear, a physician may determine that the repairing the tear with sutures is the best option for treatment. This often occurs when the tear is located in the red zone of the meniscus, where there is sufficient blood flow for the tear to heal itself. In such a situation, the suturing device 200 and suturing process described above may be used to repair the portion of the meniscus with the tear. This typically involves suturing the meniscus so that the tissue around the tear is held securely together while the biological healing process occurs. As with the replacement procedure described above, the repair procedure may advantageously be performed using arthroscopic techniques.

Figure 25:
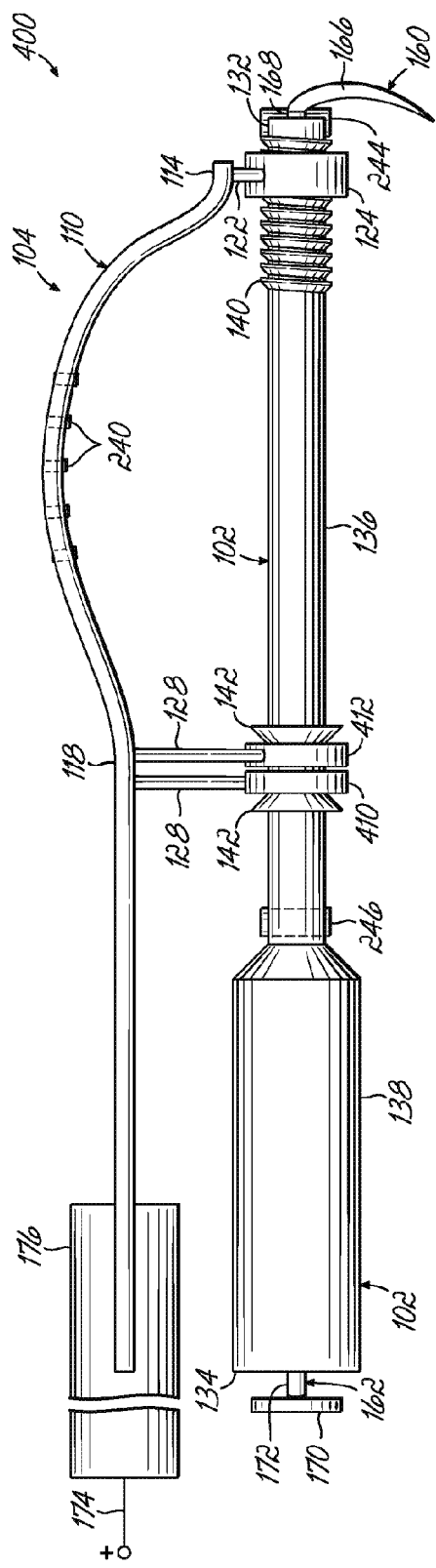
FIG. 25 is a side elevational view of a medical device according to one embodiment for cutting and suturing biological tissue.
Figure 26:
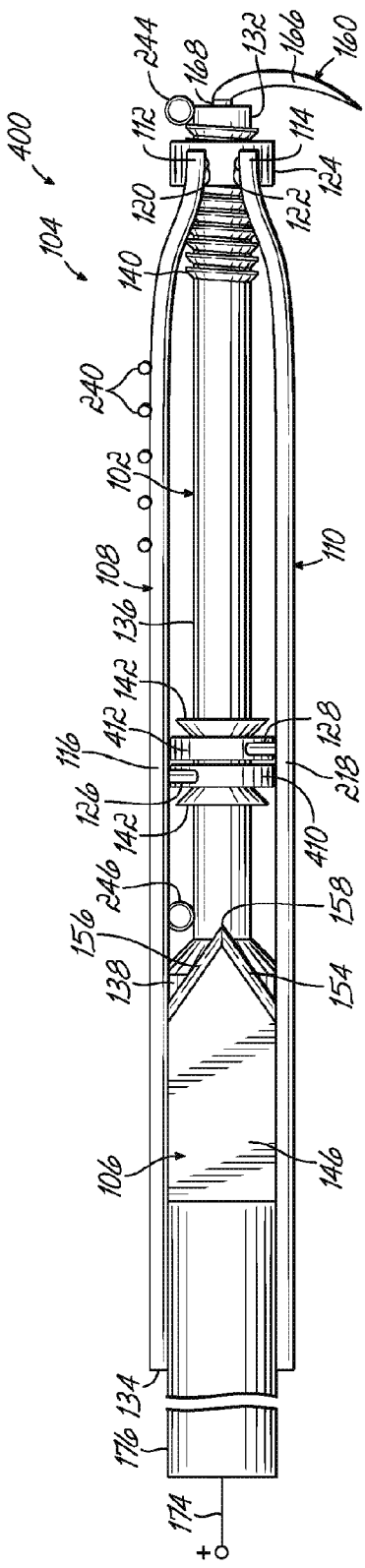
FIG. 26 is a top elevational view of the medical device of FIG. 25.

FIGS. 25 and 26 illustrate one embodiment of a medical device 400 for both cutting and suturing biological tissue. Because the medical device 400 incorporates aspects of both the cutting device 100 and suturing device 200, like reference numbers are used to refer to like structure from the embodiments of the cutting device 100 and suturing device 200 discussed above. Specifically, the medical device 400 includes the shaft 102, the attachment member 160, the first guide member 108, and the second guide member 110. The first portion 112 of the first guide member 108 is coupled to the first collar 124 by the arm 120, and the first portion 112 of the second guide member 110 is coupled to the first collar 124 by the arm 122.

Rather than including the second collar 130 retained on the shaft 102 between the horns 142, the medical device 400 includes a second collar 410 and a third collar 412 retained between the horns 142. The arm 126 couples the second portion 116 of the first guide member 108 to the second collar 410 and the arm 128 couples the second portion 118 of the second guide member 110 to the third collar 412. The second collar 410 and third collar 412 collectively function in a similar manner as the second collar 130 (FIG. 2) in that they facilitate coupling the cutting guide 104 to the shaft 102 but allow for relative rotation between the cutting guide 104 and the shaft 102. In one embodiment, the second collar 410 and third collar 412 are integrally formed so as to define first and second portions of a unitary structure (not shown) that also functions like the second collar 130. It will be appreciated that the concept of coupling the arm 126 and the arm 128 to separate collars may also be applied to either or both of the cutting device 100 and suturing device 200. Similarly, the medical device 400 may alternatively be provided with the second collar 130 (FIGS. 2-8) instead of both the second collar 410 and third collar 412.

The first guide member 108 and second guide member 110 are configured to direct the blade 106 along an arcuate cutting path, as discussed above with reference to the cutting device 100. However, because the medical device 400 also incorporates aspects of the suturing device 200, the first guide member 108 may further include the suture guides 240 in the same manner as the first guide member 208 (FIGS. 7-8).

Thus, the medical device 400 operates upon the same principles discussed above with reference to the cutting device 100 and the suturing device 200. Accordingly, reference can be made to the above description to appreciate how the medical device 400 may be used to cut and suture tissue, with the cartilage forming the medial meniscus 10 being one example of such tissue. One difference when using the medical device 400 to replace the damaged portion 44 of the medial meniscus 10 is that the cutting guide 104 may remain positioned within the knee joint 2 after the cutting operation is performed. For example, after advancing the blade 106 along the first guide member 108 and second guide member 110 to cut the damaged portion 44 from the medial meniscus, the blade 106 may be retracted and, if desired, removed completely from the cutting guide 104 and knee joint 2. The implant 44 may then be inserted into the knee joint and positioned between the first guide member 108 and second guide member 110. Additionally, the external needle guide 252 may be inserted through the first ring member 244, around the lateral surface 32 of the medial meniscus 10, and to the second ring member 246 in the same manner as described above. Once the first guide member 108 and second guide member 110 are adjusted to a desired arcuate profile with the suture guides 240 configured to direct the suture needle 242 through both the implant 46 and the medial meniscus 10, the suturing operation described above may be performed.

While the invention has been illustrated by the description of various embodiments, and while the various embodiments have been described in considerable detail, it is not the intention of the inventors to restrict or in any way limit the scope of the appended claims to such detail. Additional advantages and modifications will readily appear to those skilled in the art. For example, the external needle guide 252 may alternatively be a flexible plate (not shown) having openings and the suture thread 262 positioned on one side of the plate. Moreover, the various features of the invention may be used alone or in numerous combinations depending on the needs and preferences of the user. For instance, when suturing some types of tissue with the suturing device 200, it may be desirable to provide the suture guides 240 on both the first guide member 208 and second guide member 210. Therefore, the invention in its broader aspects is not limited to the specific details, representative apparatus and methods, and illustrative examples shown and described. Accordingly, departures may be made from such details without departing from the scope or spirit of the general inventive concept.

What is claimed is:

1. A medical device for suturing biological tissue with a suture needle, comprising:
   a shaft;
   a first guide member having an arcuate profile and configured to be positioned proximate the biological tissue, the first guide member including a first portion rotatably coupled about an outer surface of the shaft at a first location, a second portion rotatably coupled about the outer surface of the shaft at a second location, spaced from the first location, and at least one suture guide configured to direct the suture needle along a path extending through the biological tissue,
   the at least one suture guide extending from a first open end, configured to receive the suture needle, to a second open end, configured to receive the suture needle, the at least one suture guide removable from the biological tissue following suturing of the biological tissue,
   wherein the first portion of the first guide member is movable along the shaft relative to the second location, the first guide member being configured to flex upon movement of the first portion to change an arcuate profile defined laterally between the first and second locations of the shaft; and
   an external needle guide having first and second portions configured to be positioned proximate the respective first and second locations on the shaft and arranged so that the biological tissue is at least partially located between the external needle guide and the first guide member, the external needle guide being cannulated and including openings configured to receive the suture needle after the suture needle passes through the biological tissue, wherein the external needle guide includes a slot extending from a location at or near the first end to a location at or near the second end such that the external needle guide has a substantially C-shaped cross-section, the plurality of openings of the external needle guide being positioned opposite the slot.

2. The medical device of claim 1, wherein the first guide member is configured to be positioned proximate a superior surface of meniscoid biological tissue facing a femur and the at least one suture guide is configured to direct the suture needle through an intermediate portion of the meniscoid biological tissue, extending between the superior surface and an inferior surface of the meniscoid biological tissue facing a tibia.

3. The medical device of claim 1, wherein the first guide member includes a plurality of suture guides and the external needle guide includes a plurality of openings, each suture guide being configured to direct the suture needle through the biological tissue to a corresponding one of the plurality of openings.

4. The medical device of claim 1, wherein the external needle guide is configured to be positioned proximate an intermediate surface of meniscoid biological tissue, between a superior surface of the tissue facing a femur and an interior surface of the tissue facing a tibia, the first guide member is configured to be positioned proximate the superior surface, and the at least one suture guide is configured to direct the suture needle through the meniscoid biological tissue to the external needle guide.

5. The medical device of claim 1, wherein the at least one suture guide is a cylindrical tube coupled to the first guide member and aligned in a direction generally transverse to an extension of the first guide member.

6. The medical device of claim 1, wherein the at least one suture guide is asymmetrically-arranged about an axis of the shaft.

7. A medical device for suturing biological tissue with a suture needle, comprising:
    a shaft having a helically-threaded portion;
    a first collar threadably received on, and movable about, the threaded portion of the shaft;
    a second collar retained on the shaft at a location spaced from the helically-threaded portion;
    a first guide member having an arcuate profile and configured to be positioned proximate the biological tissue, the first guide member including a first portion coupled to the first collar, a second portion coupled to the second collar, and at least one suture guide configured to direct the suture needle along a path extending through the biological tissue; and
    an external needle guide, having first and second portions configured to be positioned proximate the respective first and second locations on the shaft, arranged so that the biological tissue is substantially located between a surface portion of the external needle guide facing toward the shaft and a surface portion of the first guide member facing away from the shaft,
    wherein the shaft is rotatable relative to the first guide member to move the first collar along an outer surface of the shaft relative to the second collar, the first guide member being configured to flex upon movement of the first collar to change an arcuate profile thereof.

8. The medical device of claim 7, wherein the biological tissue is a meniscus having a wedge-shaped cross-section including a superior surface facing a femur, an inferior surface facing a tibia, and a lateral surface extending between the superior and inferior surfaces, the first guide member configured to be positioned proximate the superior surface and the at least one suture guide configured to direct the suture needle through the meniscus to the lateral surface.

9. The medical device of claim 7, wherein the external needle guide is cannulated and includes openings configured to receive the suture needle after the suture needle passes through the biological tissue.

10. The medical device of claim 9, wherein the first guide member includes a plurality of suture guides and the external needle guide includes a plurality of openings, each suture guide being configured to direct the suture needle through the biological tissue to a corresponding one of the plurality of openings.

11. The medical device of claim 9, wherein the external needle guide includes a slot extending from a location at or near the first end to a location at or near the second end such that the external needle guide has a substantially C-shaped cross-section, the plurality of openings of the external needle guide being positioned opposite the slot.

12. The medical device of claim 9, wherein the biological tissue is a meniscus having a wedge-shaped cross-section including a superior surface facing a femur, an inferior surface facing a tibia, and a lateral surface extending between the superior and inferior surfaces, the external needle guide configured to be positioned proximate the lateral surface, the first guide member configured to be positioned proximate the superior surface, and the at least one suture guide configured to direct the suture needle through the meniscus to the external needle guide.

13. The medical device of claim 7, further comprising a second guide member configured to be positioned proximate the biological tissue and spaced from the first guide member, with at least some of the biological tissue positioned therebetween, the second guide member including a first portion coupled to the first collar and a second portion coupled to the second collar.

14. The medical device of claim 7, wherein the at least one suture guide is a cylindrical tube coupled to the first guide member and aligned in a direction generally transverse to an extension of the first guide member.

15. The medical device of claim 7, further comprising an attachment member including a rod and a hook coupled to the rod, the hook configured to secure to the biological tissue, wherein a portion of the rod is configured to extend through a bore in the shaft.

16. A medical device for suturing biological tissue with a suture needle, comprising:
    a shaft, wherein the shaft includes a helically-threaded portion;
    a first guide member having an arcuate profile and configured to be positioned proximate the biological tissue, the first guide member including a first portion rotatably coupled about an outer surface of the shaft at a first location, a second portion rotatably coupled about the outer surface of the shaft at a second location, spaced from the first location, and at least one suture guide configured to direct the suture needle along a path extending through the biological tissue,
    the at least one suture guide extending from a first open end, configured to receive the suture needle, to a second open end, configured to receive the suture needle, the at least one suture guide removable from the biological tissue following suturing of the biological tissue, wherein the first portion of the first guide member is movable along the shaft relative to the second location, the first guide member being configured to flex upon movement of the first portion to change an arcuate profile defined laterally between the first and second locations of the shaft;

a second guide member configured to be positioned proximate the biological tissue and spaced from the first guide member, with at least some of the biological tissue positioned therebetween, the second guide member including a first portion rotatably coupled about the shaft at the first location and a second portion rotatably coupled about the shaft at or near the second location, wherein the first portion of the second guide member is movable along the shaft relative to the second location, the second guide member being configured to flex upon movement of the first portion to change an arcuate profile defined between the first and second locations of the shaft;

a first collar threadably received by the helically-threaded portion at the first location, the first portion of the first guide member and the first portion of the second guide member coupled to the first collar; and at least a second collar received by the shaft at the second location, one or both of the second portion of the first guide member and the second portion of the second guide member coupled to the second collar, wherein the first collar is movable along the outer surface of the shaft relative to the second collar.

\* \* \* \* \*